(12) United States Patent
Subramaniam et al.

(10) Patent No.: US 10,550,383 B2
(45) Date of Patent: *Feb. 4, 2020

(54) GALVANOTAXIS ASSAY FOR QUANTITATIVE ASSESSMENT OF THE METASTATIC POTENTIAL OF CANCER CELLS

(71) Applicant: Ohio State Innovation Foundation, Columbus, OH (US)

(72) Inventors: Vish Subramaniam, Westerville, OH (US); Joseph West, Richwood, OH (US); Emily Alkandry, Columbus, OH (US); Mohd Nasser, Columbus, OH (US); Dinesh Ahirwar, Columbus, OH (US); Ramesh Ganju, Dublin, OH (US); Travis Jones, West Chester, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 44 days.

This patent is subject to a terminal disclaimer.

(21) Appl. No.: 15/887,090

(22) Filed: Feb. 2, 2018

(65) Prior Publication Data
US 2018/0171326 A1    Jun. 21, 2018

Related U.S. Application Data

(63) Continuation of application No. 14/826,487, filed on Aug. 14, 2015, now Pat. No. 9,885,031, which is a (Continued)

(51) Int. Cl.
*C12N 13/00* (2006.01)
*A61N 2/02* (2006.01)
(Continued)

(52) U.S. Cl.
CPC .............. *C12N 13/00* (2013.01); *A61N 1/40* (2013.01); *A61N 2/02* (2013.01); *A61N 2/004* (2013.01)

(58) Field of Classification Search
None
See application file for complete search history.

(56) References Cited

U.S. PATENT DOCUMENTS 6,790,330 B2    9/2004    Gascoyne et al.
7,012,100 B1    3/2006    Edwards et al.
(Continued)

FOREIGN PATENT DOCUMENTS

WO    2011063458 A1    6/2011

OTHER PUBLICATIONS

Bullock, et al. The Effect of Induced Biphasic Pulsed Currents on Re-Epithelialization of a Novel Wound Healing Model, Bioelectromagnetics vol. 28 No. 1, Jan. 1, 2007, pp. 31-41.
(Continued)

*Primary Examiner* — David W Berke-Schlessel
(74) *Attorney, Agent, or Firm* — Standley Law Group LLP

(57) ABSTRACT

An apparatus and method for accelerating and/or inhibiting the migration of cells by applying a time-varying magnetic field to induce eddy currents that promote electrotaxis (galvanotaxis) of cells without the need for chemokines or glucose. The present invention can also be used to study and quantify the metastatic potential of different cell lines.

30 Claims, 30 Drawing Sheets

Related U.S. Application Data continuation-in-part of application No. 14/765,993, filed as application No. PCT/US2014/014779 on Feb. 5, 2014, now Pat. No. 9,809,810.

(60) Provisional application No. 61/760,987, filed on Feb. 5, 2013.

(51) Int. Cl.
*A61N 1/40* (2006.01)
*A61N 2/00* (2006.01)

(56) References Cited

U.S. PATENT DOCUMENTS

| | | |
|---|---|---|
| 7,117,034 B2 | 10/2006 | Kronberg |
| 7,700,615 B2 | 4/2010 | Edwards et al. |
| 8,019,414 B2 | 9/2011 | Palti |
| 9,809,810 B2 | 11/2017 | Subramaniam et al. |
| 9,885,031 B2 | 2/2018 | Subramaniam et al. |
| 2004/0152067 A1 | 8/2004 | Wang et al. |
| 2006/0276858 A1 | 12/2006 | Palti |
| 2008/0299086 A1 | 12/2008 | Kanzaki et al. |
| 2009/0018613 A1 | 1/2009 | Brighton |
| 2010/0273258 A1 | 10/2010 | Lannutti et al. |
| 2010/0298624 A1 | 11/2010 | Becker |
| 2011/0194979 A1 | 8/2011 | Chin et al. |
| 2012/0035457 A1 | 2/2012 | Subramaniam et al. |
| 2012/0064594 A1 | 3/2012 | Van Bree et al. |
| 2013/0034899 A1 | 2/2013 | Takemura et al. |
| 2016/0340635 A1 | 11/2016 | Kirshner et al. |
| 2019/0161722 A1 | 5/2019 | Nagatomi et al. |

OTHER PUBLICATIONS

Song, et al. Application of Direct Current Electric Fields to Cells and Tissues in Vitro and Modulation of Wound Electric Field in Vivo. Nature Protocols. vol. 2 No. 6, Jun. 2007, pp. 1479-489.

Vianale, et al. Extremely Low Frequency Electromagnetic Filed Enhances Human Keratinocyte Cell Growth and Decreases Proinflammatory Chemokine Productions. British Journal of Dermatology. vol. 158 No. 6, Jun. 2008, pp. 1189-1196.

Djamgoz, Mustafa B. A. et al., Directional Movement of Rat Prostate Cancer Cells in Direct-Current Electric Field: Involvement of Voltage-Gated Na+ Channel Activity, Journal of Cell Science 114 (14), 2001, pp. 2697-2705.

Fraser, Scott P. et al., Voltage-Gated Sodium Channel Expression and Potentiation of Human Breast Cancer Metastasis, Clinical Cancer Research 11, Aug. 1, 2005, pp. 5381-5389.

Hart, Francis X. et al., Keratinocyte Galvanotaxis in Combined DC and AC Electric Fields Supports an Electromechanical Transduction Sensing Mechanism, Bioelectromagnetics 34, Feb. 2013, pp. 85-94.

Yan, Xialong. et al., Lung Cancer A549 Cells Migrate Directionally in DC Electric Fields with Polarized and Activated EGFRs, Bioelectromagnetics 30, 2009, pp. 29-35.

Sun, et al., Electrotaxis of lung cancer cells in ordered three-dimensional scaffolds, Biomicrofluids 6, 2012.

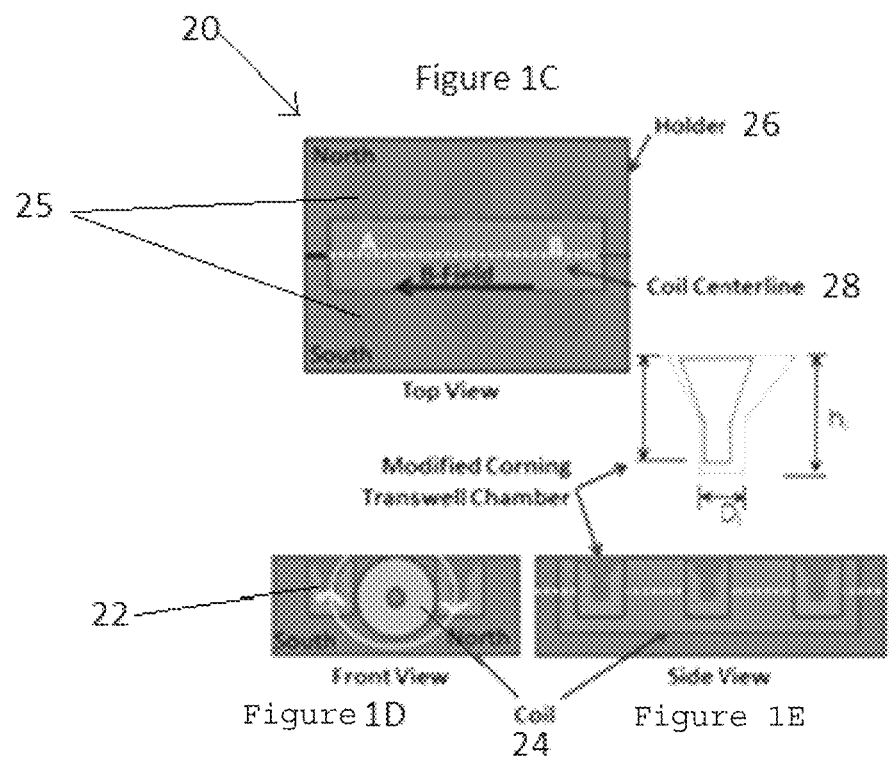

Figure 6A
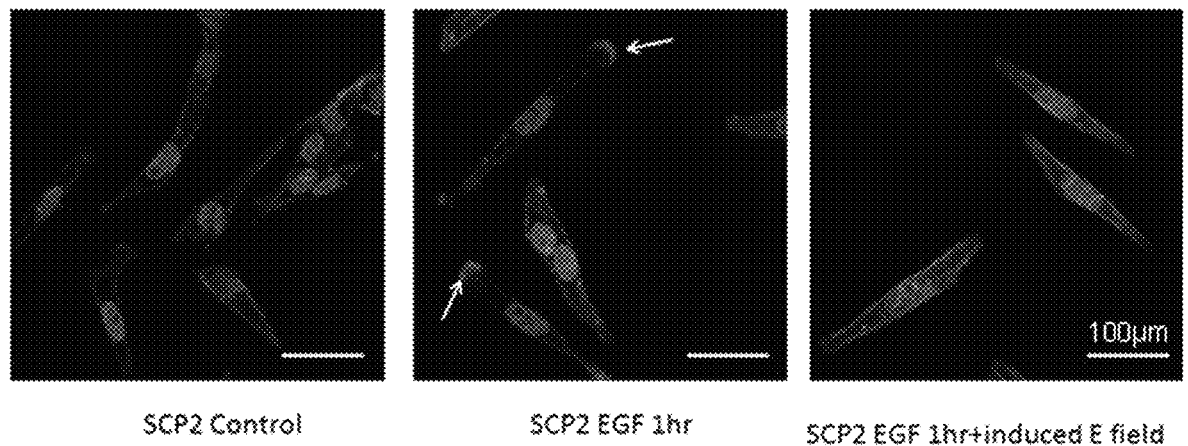
SCP2 Control    SCP2 EGF 1hr    SCP2 EGF 1hr+induced E field
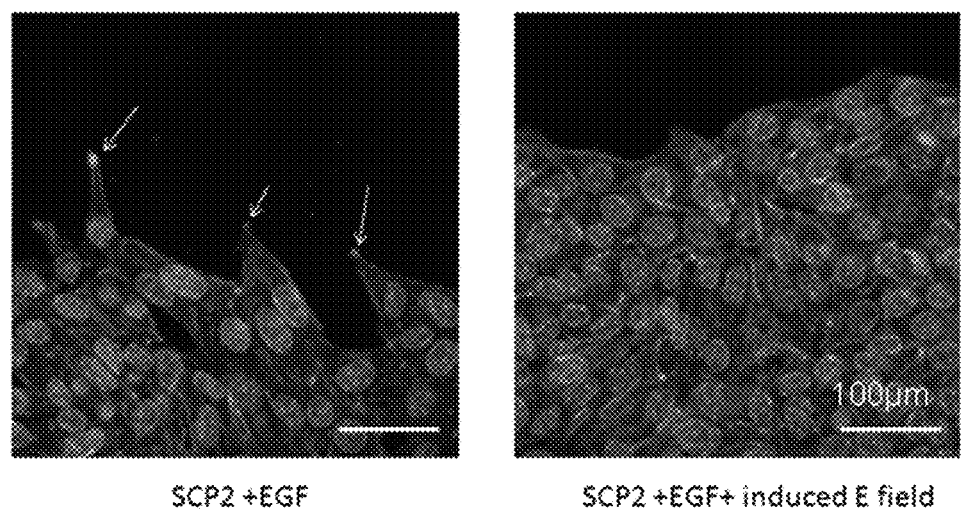
SCP2 +EGF    SCP2 +EGF+ induced E field
Figure 6B

GALVANOTAXIS ASSAY FOR QUANTITATIVE ASSESSMENT OF THE METASTATIC POTENTIAL OF CANCER CELLS

CROSS-REFERENCE TO RELATED APPLICATIONS

This application is a continuation of U.S. application Ser. No. 14/826,487, filed Aug. 14, 2015, which is a continuation-in-part of U.S. application Ser. No. 14/765,993, filed Aug. 5, 2015, which is the U.S. national stage entry of International Application No. PCT/US14/14779, filed Feb. 5, 2014, which claims priority to U.S. Provisional Application No. 61/760,987, filed on Feb. 5, 2013, each of which is herein incorporated by reference in its entirety.

BACKGROUND OF THE INVENTIVE FIELD

The present invention is directed to an apparatus and method of accelerating and/or inhibiting metastasis of cells by subjecting the cells to an electric field. More particularly, the present invention is directed to an apparatus and method for accelerating and/or inhibiting metastasis of cancer cells by applying a time-varying magnetic field to induce electric fields that promote or hinder electrotaxis (galvanotaxis) of cells without the need for chemokines or glucose.

SUMMARY OF THE GENERAL INVENTIVE CONCEPT

In a preferred embodiment of the present invention, a time-varying magnetic field from an electromagnetic (EM) coil is used to induce electric fields in a modified version of Corning's Transwell transmembrane permeable assay. By varying the characteristics of the excitation of the EM coil and the direction of application of the electric field, it is possible to enhance cell migration as well as hinder it, in the presence or absence of chemokines. The modified assay provides a novel method to study and quantify metastasis. For example, metastatic cell lines can be compared to each other in these assays by subjecting them to the EM fields and counting the number of cells that migrate across the permeable membrane. Comparisons between cell lines can also be drawn and quantified in the presence of both EM fields and chemokines. Quantification can be accomplished by counting the cells or by digitizing the image and calculating cell coverage areas on the bottom of the membrane. In one embodiment, the EM coil is driven using a function generator using a 20 Vpp, 100 kHz, sawtooth wave with a sharp ~50 ns drop to generate a rapidly time-varying magnetic field.

In an exemplary embodiment of the present invention, the method is comprised of the steps of:
  providing an electromagnetic coil having a first end and a second end;
  connecting the electromagnetic coil to a function generator;
  applying a time-varying sawtooth voltage waveform to the electromagnetic coil;
  inducing a time-varying electric field around the electromagnetic coil;
  placing the electromagnetic coil adjacent to the location of cancer cells with the direction of the induced electric field directed towards the cancer cells;
  orientating the placement of the electromagnetic coil so that the direction of the electric field is directed away from an area of healthy cells; and
  hindering migration of the cancer cells using the induced electric field.

In one embodiment the waveform applied to the coil is a 20 volts peak to peak, 100 kHz sawtooth waveform with a 50 ns drop off at its trailing edge that induces a rapidly time-varying magnetic field.

It is appreciated that the characteristics of the waveform can be adjusted to control metastasis.

Furthermore, the following additional steps may be taken according to one embodiment of the invention for studying and quantifying the metastatic potential of cell lines:
  placing the electromagnetic coil in between a first row of a plurality of assay wells and second row of a plurality of assay wells;
  providing a plurality of well inserts having a porous membrane;
  placing one of the well inserts into each of the plurality of assay wells so that the wells are divided into a lower and upper compartment;
  placing a medium into each of the plurality of assay wells;
  placing a predetermined line of cancer cells into each of the assay wells;
  allowing the predetermined lines of cancer cells to settle on top of the porous membranes;
  taking an image of the porous membrane after the step of inducing a time-varying electric field;
  quantifying metastatic potential of the predetermined lines of cancer cells; and
  introducing a predetermined chemokine into each of the assay wells.

The foregoing and other features and advantages of the present invention will be apparent from the following more detailed description of the particular embodiments, as illustrated in the accompanying drawings.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein:

FIGS. 1c (top view), 1d (front view), and 1e (side view) illustrate one embodiment of the apparatus of the present invention having an EM coil placed between two rows of wells;

FIGS. 6a and 6b illustrate the visualization of actin filaments by fluorescence microscopy;

FIGS. 18a and 18b illustrate charts showing the average intensity of actin fluorescence versus length along isolated cells shown in the left panel of FIG. 6a;

FIGS. 19a and 19b illustrate charts showing the average intensity of actin fluorescence versus length along isolated cells shown in the middle panel of FIG. 6a;

FIGS. 20a, 20b, and 20c illustrate charts showing the average intensity of actin fluorescence versus length along isolated cells shown in the right panel of FIG. 6a;

DETAILED DESCRIPTION OF EXEMPLARY EMBODIMENT(S)

Figure 1A:
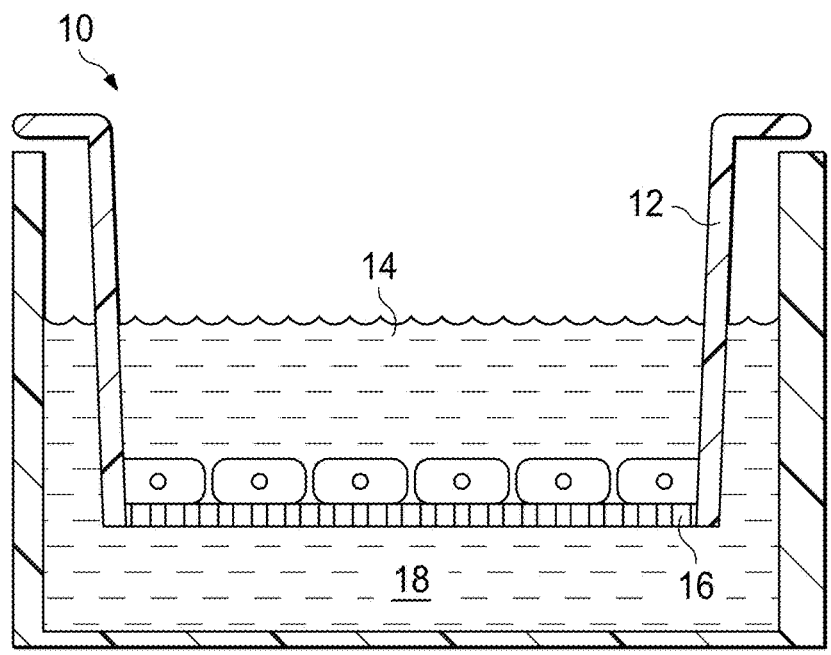
FIG. 1a illustrates an assay with an insert with a porous membrane.

An assay that is commonly used to evaluate the response of cancer cells to chemokines and chemotherapy drugs is Corning's Transwell Permeable Support assay 10. In this assay, inserts 12 with porous membranes 16 at the bottom are placed into standard plate wells as shown in FIG. 1a. After coating the bottom of the membrane with fibronectin, and with a suitable chemokine placed in the lower compartment 18, a monolayer of cells can be made to migrate from the upper compartment 14 to the lower compartment. In other words, by placing suitable chemokines in the lower compartment, the infiltration capabilities of cancer cells may be studied by observing the number that migrate from the membrane side in contact with the upper compartment to the membrane side in contact with the lower compartment. This is an example of chemotaxis, which refers to the motility of cells under the action of a gradient in the concentration of a chemical substance such as growth factors or chemokines. Biological cells move in response to other forces as well, such as electrical forces. The directional movement of biological cells in the presence of an applied electric field is known as Galvanotaxis or electrotaxis. This effect is named after Luigi Galvani, who in the 18$^{th}$ century discovered bioelectricity. The majority of experiments related to galvanotaxis over the past two centuries have involved steady electric fields applied via electrodes placed in contact with the medium containing cells (usually, the electrodes are in contact with the medium containing the cells through agar filled tubes and the applied electric field is usually DC).

The system and method of the present invention is used for inducing electric fields in the medium containing cells, for example the Corning's Transwell permeable assay, by applying time-varying magnetic fields. The method uses electromagnetic (EM) induction to induce electric fields and eddy currents in the medium to promote or hinder galvanotaxis of cells without the need for chemokines or glucose. Hindrance is of significance since cancer cells are known to respond to externally applied electric fields so that they can be distinguished from normal cells. Moreover, metastatic potential of different cancer cells may be quantitatively evaluated by counting the number of cells migrated across the membrane, so that this can form the basis for a new assay.

In one embodiment, a SCP2 cell line cultured in Dulbecco's Modified Eagle Medium (DMEM) with a density of $3.3 \times 10^6$ cells/mL is used. This cell line is a highly metastatic estrogen receptor (negative) breast cancer cell line derived from the MDA-MB-231 cell line. In this embodiment, 150 μL of the medium containing this cell line (~$4.95 \times 10^4$ cells) is pipetted into the upper compartment of a single Transwell permeable insert (equipped with a 6 µm filter) while the lower compartment has 200 µL of the same medium but with no cells. The single plate well with the insert is then placed adjacent to a horizontally oriented electromagnetic (EM) coil (R ~22Ω, L=10 mH) and fixture as shown in FIGS. 1c-1e.

FIGS. 1c, 1d, and 1e illustrate schematics of one embodiment of the apparatus 20 of the present invention with modified Corning Transwell plates 22 with the electromagnetic (EM) coil 24 placed in the middle of two rows 25 of wells. These components are placed in a holder 26 as shown. The center line 28 of the coil is illustrated by the dashed line as shown. The induced electric field is shown in FIG. 1d as the circle drawn around the coil. The glass wells are preferably configured with offset holes to accommodate Corning Transwell permeable inserts with dimensions such that the centerline of the coil is at the same elevation as the membrane of the insert. FIG. 1c illustrates a top view of the apparatus. FIG. 1d illustrates a front view and FIG. 1e illustrates a side view. In another embodiment, a single well with one insert is used, adjacent to the coil. Once the cells are allowed to settle onto the upper surface of the permeable membrane (see FIG. 1a), the entire apparatus is placed inside an incubator (at 37° C. with 5% $CO_2$) for a period of 12 hours. As control case, a similar plate well with similar permeable insert and with the same highly metastatic cells, but not exposed to the EM coil, is also placed in the incubator. Both setups are imaged after a period of 12 hours.

In one embodiment, the EM coil is driven using a function generator using a 20 Vpp, 100 kHz, sawtooth wave with a sharp ~50 ns drop to generate a rapidly time-varying magnetic field with components $B_r$ and $B_z$. By Faraday's law these temporally varying magnetic fields from the EM coil induce an electric field $E_\theta$ in the medium containing the cells due to the small but non-zero electrical conductivity of the medium. Because of the placement of the plate well relative to the coil, this results in a vertically directed electric field across the membrane, but with $E_\theta$ decaying radially with increasing distance from the coil. At the driving frequency of 100 kHz, $E_\theta$ switches directions back and forth (up and down) across the membrane, but with a component directed downward or upward for non-equal portions of a duty cycle, depending on the side of the coil.

Application of the time-varying magnetic field results in induced electric fields in the appropriate direction which increases migration of the metastatic cancer cells across the membrane even in the absence of chemokines. In contrast, the control case (with no applied electric field) results in the typically observed random migration patterns. By selecting a different set of characteristics for the driving waveform (e.g. waveform type, peak to peak voltage, and frequency) migration of cells can be reduced by simply reversing the field. It should be noted that this result is of significance for cancer treatment where inhibition of metastasis in tumors may have beneficial effects in vivo.

In addition to implications for hindering metastasis, Corning's Transwell assay can be modified to provide a method to quantify metastasis. For instance, metastatic cell lines can be compared to each other in these assays by subjecting them to the same EM fields and counting the number of cells that migrate across the permeable membrane. The quantification can be accomplished by counting the cells or by digitizing the image and calculating cell coverage areas on the bottom of the membrane. The effects of various drugs and chemokines may also be evaluated in the presence of EM fields so as to decipher the effects of in vivo endogenous electric fields that may adversely affect the therapeutic effects of chemotherapy drugs.

In summary, a time-varying magnetic field from an electromagnetic (EM) coil is used to induce electric fields in a modified version of Corning's Transwell permeable assay. Preliminary in vitro experiments on the highly metastatic SCP2 breast cancer cell lines show that cell migration across the membrane can be significantly increased compared to the control case where no EM field is applied. By varying the characteristics of the excitation of the EM coil, it is possible to accelerate metastasis as well as hinder it. This degree of control without the use of chemokines suggests a natural means of quantifying the metastatic potential of different cancer cells as well as a natural means of comparing them with the motility of normal cells.

The present invention also relates to a method to induce electric fields and drive electrotaxis (galvanotaxis) without the need for electrodes to be in contact with the media containing the cell cultures. The following experimental results were obtained using a modification of the transmembrane assay, demonstrating the hindrance of migration of breast cancer cells ($SCP_2$) or (SCP2) when an induced a.c. electric field is present in the appropriate direction (i.e. in the direction of migration). Of significance is that migration of these cells is hindered at electric field strengths many orders of magnitude (5 to 6) below those previously reported for d.c. electrotaxis, and even in the presence of a chemokine (SDF-1α) or a growth factor (EGF).

Induced a.c. electric fields applied in the direction of migration are also shown to hinder motility of non-transformed human mammary epithelial cells ($MCF_{10}A$) or (MCF10A) in the presence of the growth factor EGF. In addition, as discussed below, the method of the present invention can be applied to other cell migration assays (scratch assay). Furthermore, the present invention demonstrates that by changing the coil design and holder, the method is also compatible with commercially available multi-well culture plates.

Cell migration is important in several physiologically relevant situations such as embryonic development, wound healing, and metastasis of cancer. Non-ciliated cells migrate in response to gradients in chemical composition (chemotaxis), mechanical forces, and electric fields (galvanotaxis or electrotaxis). The latter has been observed for over a hundred years since the report of Dineur in 1892, where the author proposed the use of the term galvanotaxis to describe migration of leukocytes in the presence of a d.c. electric field.

Since Dineur's report, many vertebrate cells have been observed to exhibit galvanotaxis or electrotaxis as it is now called. The majority of in vitro electrotaxis experiments are conducted under the action of a d.c. field, and involve metal electrodes directly inserted into the medium containing the cells or in indirect contact through agar or salt bridges. The threshold for cells to sense an electric field in vitro has been reported to be >10 mV/cm, with magnitudes of d.c. electric fields on the order of 0.1-10 V/cm required for observing electrotaxis. At these electric field strengths, effects of localized heating can be non-negligible.

Recently, electrotaxis experiments in a.c. fields of very low frequencies on the order of mHz, and a.c. fields from 1.6 Hz to 160 Hz applied together with d.c. fields have been reported. These experiments show that collective cell migration, direction of cell migration and migration speed can all be controlled by application of electric fields. Despite the use of modern patterning techniques for shaping d.c. electric fields and use of microfluidic devices, the methods of applying these d.c. and very low-frequency a.c. electric fields still involve either direct contact or indirect contact (via agar bridges) with the media containing the cells. Since the methods of applying electric fields have changed little over the past several decades, there is a need for new electrotaxis assays and methods of applying electric fields in a non-contact manner.

As described herein, a well-known assay for chemotaxis referred to as the transmembrane or Transwell assay may be modified to conduct non-contact electrotaxis experiments. The transmembrane assay was first described by Boyden to analyze the chemotactic response of leukocytes and is sometimes referred to as the Boyden chamber assay. This assay consists of an insert at the bottom of which is a membrane of selectable pore size (0.4 µm-12 µm), depending on the size of the cells. The insert is then placed into a well, forming two distinct compartments separated by the membrane. Cells are seeded on the top side of the membrane, and the bottom compartment may contain a chemotactic agent. The cells migrate from the top surface of the membrane through to the bottom surface. After a suitable incubation time (dependent on cell type), the number of migrated cells is counted by fixing and staining, or by staining fluorescently, removing from the membrane by dissociation (e.g. by using trypsin) and using a fluorescent reader.

The standard transmembrane assay may be modified to develop a new method for inducing a.c. electrotaxis in a truly non-contact manner, without the need for electrodes and agar or salt bridges to be in contact with the medium containing the cells. Moreover, this new system and method enables the study of electrotactic behavior alone or electrotaxis in the presence of chemotactic agents as well. The a.c. electric fields are induced in the media containing the cells using electromagnetic induction. A time-varying current driven through a custom designed coil placed with glass wells (with membrane inserts) lining either side of the coil enable an electric field to be induced in the vertical direction, along the axis of migration. The time-varying current generates a time-varying magnetic field which induces an electric field in the azimuthal direction around the coil. When the glass wells containing the membrane inserts are placed on the sides of the coil, this azimuthal field is in the direction perpendicular to the membranes and along the axis of migration. Results are presented for a highly metastatic human breast cancer cell line as well as for a non-transformed human mammary epithelial cell line ($MCF_{10}A$) (FIGS. 21-22), for a single duty cycle of 100 kHz as illustrative examples. The modification of the method can induce electric fields in a non-contact manner in standard culture plate wells, enabling visualization of actin filaments using phalloidin-fluorophore conjugates and fluorescence microscopy, and extending applicability of this method to the scratch migration assay as well.

FIGS. 1c-1e illustrate one embodiment of a transmembrane assay modified to incorporate an electromagnetic (EM) coil to induce electric fields to drive electrotaxis. FIG. 1c illustrates a top view of the modified transmembrane assay showing the custom-made glass wells, 3D printed holder apparatus, and an EM coil. (FIGS. 1c-e). Schematics showing the top, front, and side views of the modified transmembrane assay including EM coil and glass wells custom-made to incorporate commercially available Transwell membrane inserts. Also shown in the front view of the apparatus is the direction of the induced electric field applied over a majority (60%) of the 10 µs period.

Using the present invention, it was determined that weak a.c. electric fields hinder migration of highly metastatic $SCP_2$ cells. In one embodiment, the experimental apparatus was comprised of a EM coil, holder, glass wells that can accommodate commercially available Transwell permeable inserts (e.g., 8 µm pore, 24-well, Corning-Costar, Lowell, Mass.), and a function generator (Hewlett Packard 33120A). In this embodiment, the coil has a d.c. resistance of 50.45Ω, and an inductance of 14.25 mH as measured by an LCR meter (Extech Instruments Model 380193) at 1 kHz. The coil is placed at the center of the holder with six glass wells on either side (FIGS. 1c-1e, FIGS. 7-8). The glass wells preferably have off-centered holes within which commercially available Transwell membrane inserts can be placed at closest proximity to the coil (FIGS. 1c-1e, FIG. 7). The wells and holder are designed and fabricated so that each membrane of the transmembrane insert is positioned at the same height as the centerline of the coil. One side of the coil is arbitrarily labeled "North" for ease of reference while the other is labeled "South", with respect to the red wire labeled "East".

Figure 9:
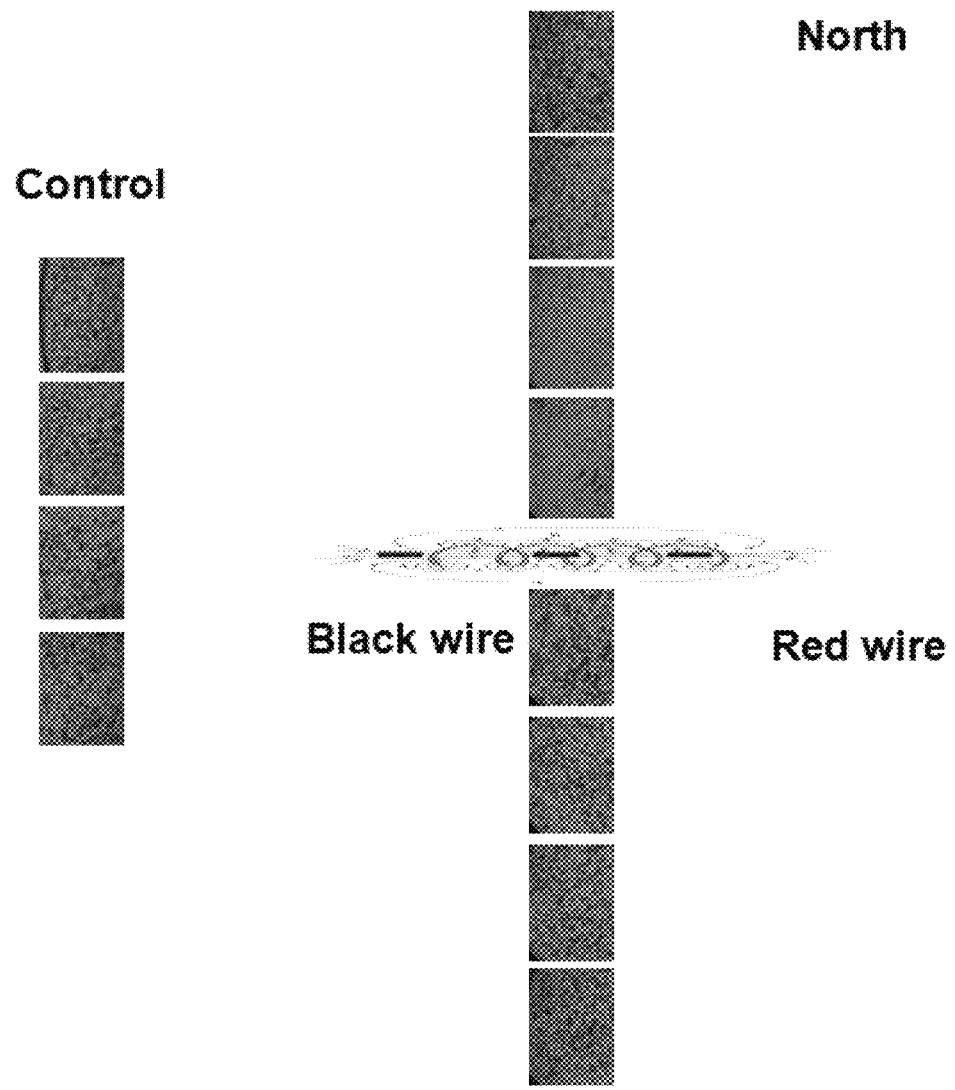
FIG. 9 illustrates one embodiment of representative fields (4 each) from the Transwell transmembrane assay and the modified transmembrane assay with SCP2 cells fixed and stained showing how the cells are counted in one embodiment of the invention.
Figure 10:
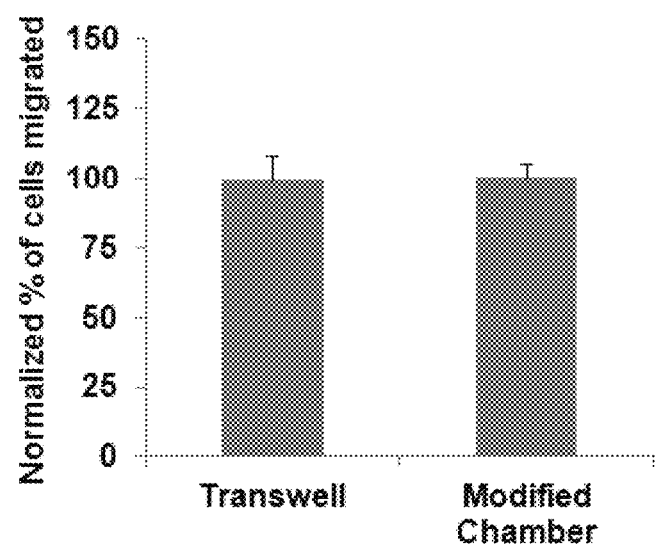
FIG. 10 illustrates how the modified transmembrane assay with the Transwell membrane inserts reproduces cell migration observed in the multi-well plates with the same inserts.

Highly metastatic breast cancer cells known as $SCP_2$, a single cell population derived from MDA-MB-231 that is known to metastasize to the bone, were cultured in Dulbecco's Modified Eagle Medium (DMEM; Life Technologies, Gaithersburg, Md., USA), supplemented with 10% heat inactivated fetal bovine serum (FBS), 5 U/mL penicillin, and 5 mg/mL streptomycin. The $SCP_2$ cells were placed in the upper chamber, and both compartments contained 0.1% FBS-DM. The entire apparatus (holder, coil, modified transmembrane chambers with Transwell inserts and cells) was placed in a 37° C. culture incubator with humidified air containing 5% $CO_2$. The leads of the coil were connected to the function generator placed outside the incubator. The cells were allowed to migrate for 8 hours, and then were fixed and stained using Hema-3 stain kit according to the manufacturer's instructions. The number of migratory cells per membrane was then measured using light microscopy by counting the total number of cells in each of five contiguous images spanning radially outward (five fields) from the coil (FIG. 9). The counts were used to determine the normalized percentage of migration, with the number of cells migrated in the control set to 100%. In order to ensure that cell migration in the modified transmem-brane assay with the Transwell insert is not statistically different from the conventional transmembrane assay, control experiments were performed (FIG. 10).

In one embodiment, a 20 Vpp, 100 kHz sawtooth shaped voltage waveform (FIG. 2a) was imposed on the coil, resulting in a time-varying current flow generating a time-varying magnetic field. In accordance with Faraday's Law, the time-varying magnetic field induces an electric field. This induced electric field can be calculated and is in the azimuthal direction (vertically up or down with respect to the membrane inserts). The induced electric field is asymmetric over a duty cycle (FIG. 2b), resulting in different durations of the electric field in the direction of migration on the two sides of the coil. On the side of the coil labeled "North", the induced electric field is in the direction of migration (i.e. downward) over ~60% of a single duty cycle lasting 10 µs with a maximum magnitude of ~2.3-2.4 µV/cm (FIG. 2b-2e). Over the remaining 40% of the 10 µs period, the induced electric field on the "North" side is in the direction opposite to that of migration (i.e. upward) with a maximum magnitude of ~(−)3.7-(−)3.8 µV/cm (FIG. 2b-2e). The opposite of these trends is realized on the side labeled "South". At any instant of time, the induced electric field decreases with increasing radial distance from the outer surface of the coil (FIG. 2c). Contours of the calculated induced electric field reveal that it is fairly uniform over the length of the coil so that each of the three wells on a given side of the coil experiences the same induced electric fields at a given instant of time (FIGS. 2d and 2e). In this embodiment, the maximum induced electric fields are on the order of ~3.8 µV/cm, at least four to five orders of magnitude smaller than typically required for electrotaxis and six orders of magnitude smaller than previously reported for MDA-MB-231 cells.

Experimental results with SCP2 cells indicate that migration on the "North" side of the coil is hindered (p=0.021) when compared to the control experiments where no electric field is present. However, migration on the "South" side of the coil shows a trend of increased migration which is not statistically significant (p=0.076) when compared to the controls where no electric field is present (FIG. 2f). Since the "North" side of the coil experiences an electric field in the direction of migration (i.e. downward) for a greater duration (~6 µs per period) compared to experiencing an electric field opposite to the direction of migration (~4 µs per period), it can be seen that migration of SCP2 cells is hindered when the induced electric field (across the membrane) is in the direction of migration. This observed hindrance of migration on the "North" side is consistent with previously reported observations that MDA-MB-231 cells migrate toward the positive electrode when subjected to d.c. electric fields.

Figure 2A:
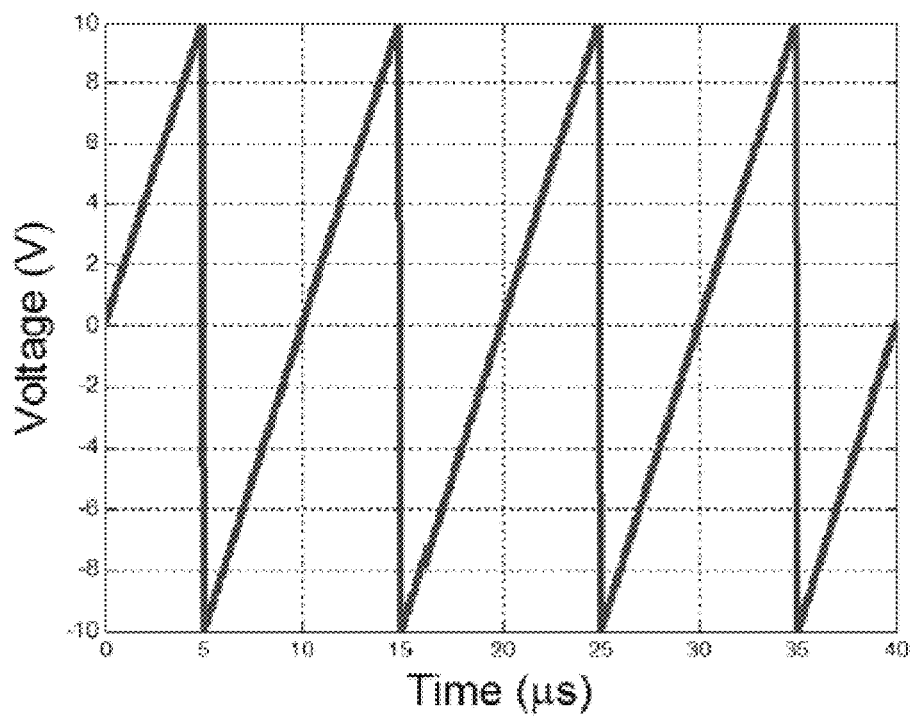
FIG. 2a illustrates a sawtooth waveform applied to the coil in one embodiment of the invention.
Figure 2B:
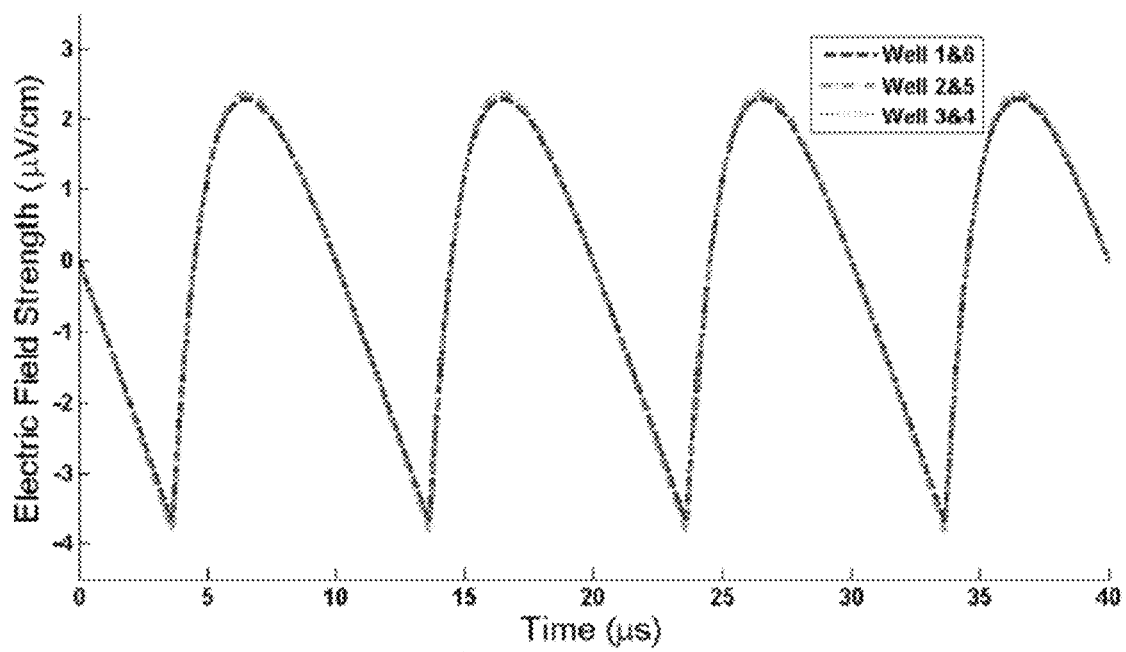
FIG. 2b illustrates a chart showing the induced electric field asymmetric over a duty cycle for one embodiment of the invention.
Figure 2C:
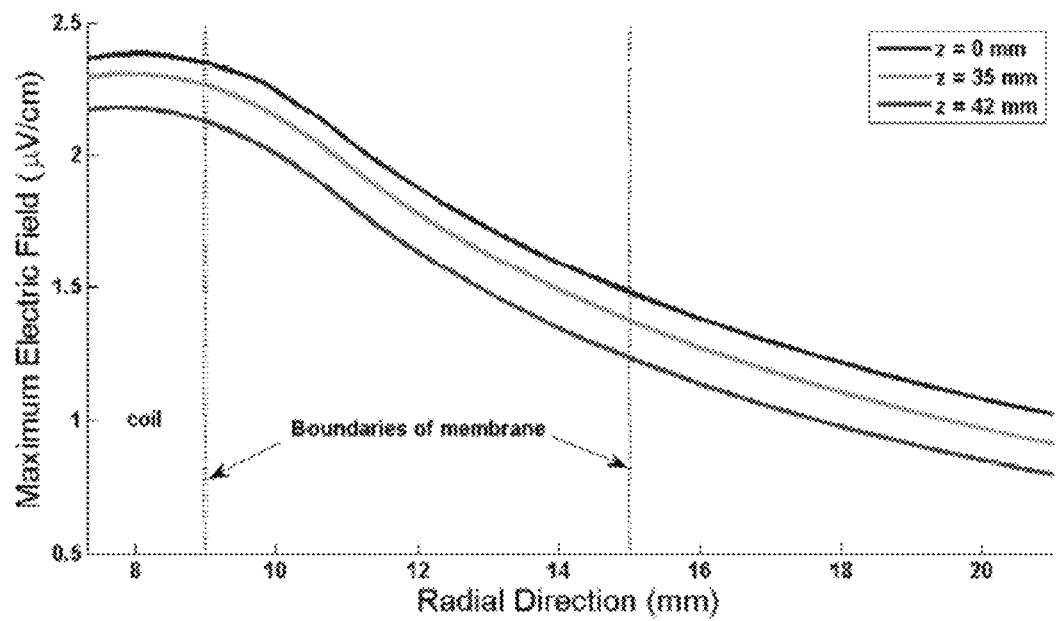
FIG. 2c illustrates a chart showing a induced electric field decreasing with increasing radial distance from the outer surface of the coil for one embodiment of the invention.
Figure 2D:
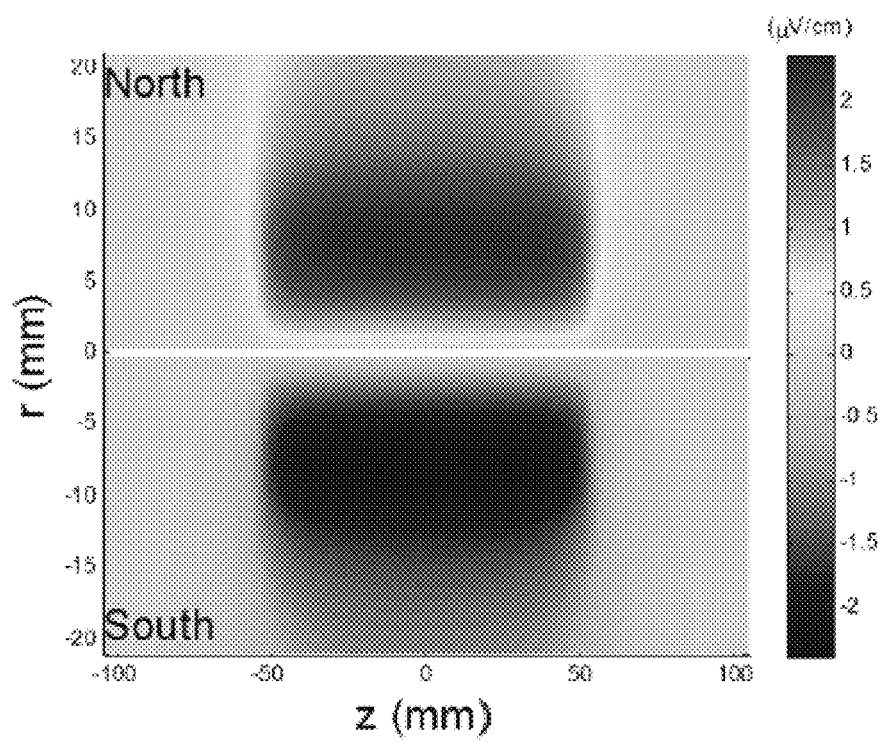
FIGS. 2d and 2e illustrate charts showing contour charts of induced electric field for one embodiment of the invention.
Figure 2E:
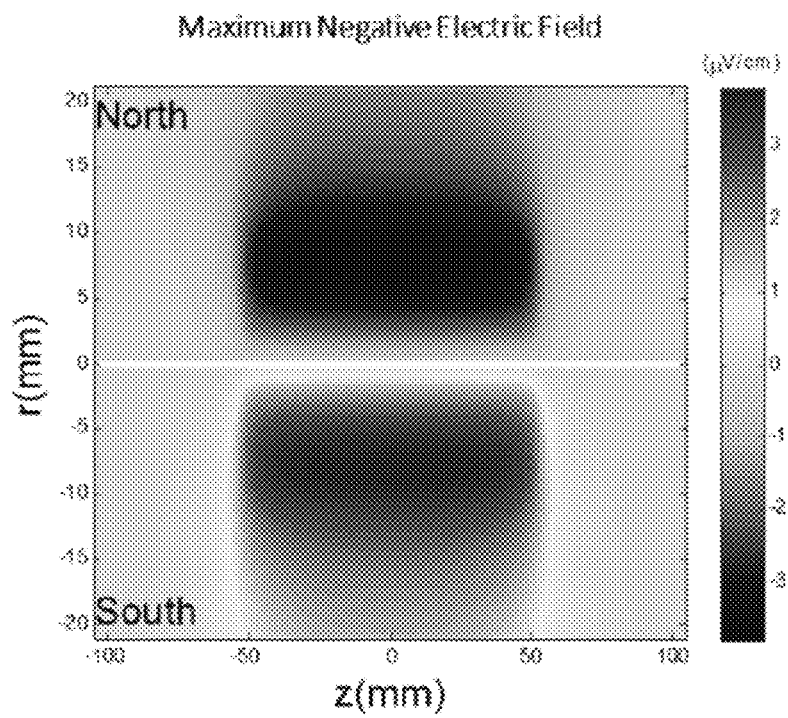
Figure 2F:
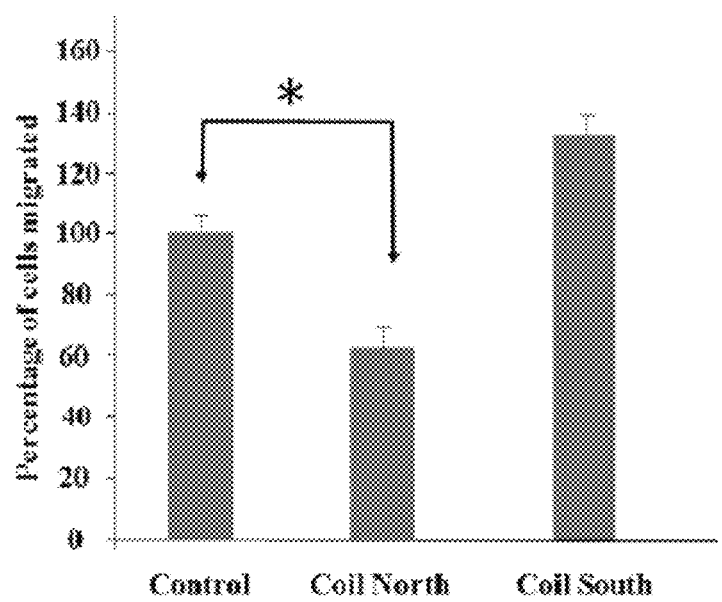
FIG. 2f illustrates a chart showing cell migration based on induced electric field for one embodiment of the invention.

FIG. 2a illustrates one embodiment of a sawtooth shaped voltage waveform output from the function generator used to drive current through the EM coil. The sharp drop-off occurs in ~50 ns. FIG. 2b illustrates the time variation of the induced azimuthal electric field $E_\theta$ calculated from first principles (see e.g., FIGS. 13-17), for all wells in the described embodiment. This induced E field is in the vertical direction (up or down) at the membrane inserts placed on either side of the coil. In this embodiment, the asymmetry over a given 10 µs interval (positive ~60% of the time and negative ~40% of the time over the interval). Based on the direction of the windings of the coils in this embodiment, a positive $E_\theta$ indicates that the induced E field is in the downward direction on the "North" side of the coil while a negative $E_\theta$ indicates an upwardly directed induced E field on the "North" side of the coil. FIG. 2c illustrates variation of the maximum $E_\theta$ versus radial distance away from the coil (i.e. along the porous membrane) calculated for each axial location where the glass wells are placed. FIG. 2d illustrates a contour plot of the induced E field on both sides of the coil where the wells are placed, for ~60% of each 10 µs period. FIG. 2e illustrates a contour plot of the induced E field on both sides of the coil, for ~40% of each 10 µs period. FIG. 2f illustrates results showing effects of induced E fields on migration of SCP2 cells (N=3). In this embodiment, the migration is hindered on the "North" side of the coil (p=0.021) while it follows a weak trend of enhanced migration on the "South" side with a borderline non-significant p value (p=0.076). The induced E field is directed downward (in the direction of migration) for ~60% per period while it is directed upward (against the direction of migration) for ~40% per period on the "North" side of the coil. These values are reversed for the "South" side of the coil.

Effects of hindered migration of SCP2 cells under weak a.c. fields are reversible. The observed hindrance of migration of SCP2 cells under the action of weak (~1 µV/cm) induced electric fields raises the question of whether or not the ability of these cells to migrate is permanently affected after exposure to the induced electric field. In order to address this question, SCP2 cells were prepared as described before, in 0.1% serum media and control experiments were separately conducted in the modified trans-membrane assay without application of the induced electric field, for 8 hours and 16 hours respectively (8 hr control (1) and 16 hrs control (4), FIG. 3). In parallel, SCP2 cells were subjected to an induced electric field generated by a sawtooth voltage waveform at 20 Vpp and 100 kHz duty cycle on the "North" side of the coil for 8 hours (8 hrs+E (2), FIG. 3, p<0.001 for 8 hrs control (1) and 8 hrs+E (2)) and a separate set which were subjected to the electric field ("North" side) for 8 hours after which time the electric field was turned off and migration allowed to continue for another 8 hours (8 hrs+E 8 hrs−E (3), FIG. 3, p<0.001 for 8 hrs control (1) and 8 hrs+E 8 hrs−E (3)). It can be seen from these results that as discussed before (FIG. 2f), application of the induced electric field in the direction of migration hinders SCP2 cell movement (8 hrs control (1) versus 8 hrs+E (2), FIG. 3).

Figure 3:
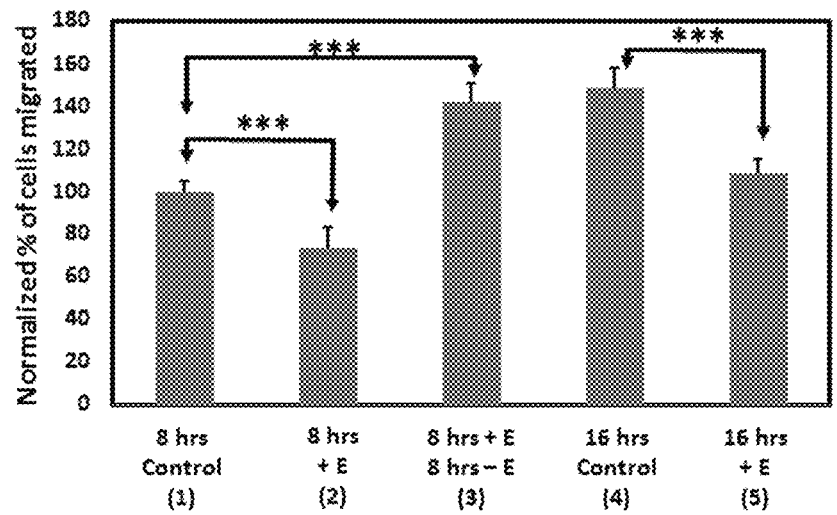
FIG. 3 illustrates a chart showing normalized percentage of cells migrated for one embodiment of the invention.

However, once the electric field is turned off after 8 hours, it can be seen that the SCP2 cells migrate over the next 8 hours in numbers comparable to the corresponding control case (8 hrs+E 8 hrs−E (3) versus 16 hrs control (4), FIG. 3, p=0.342 for 8 hrs+E 8 hrs−E (3) and 16 hrs control (4)). Furthermore, migration when exposed to the induced electric field for 16 hours is hindered compared to both the control (no induced electric field for 16 hours) and the case where the induced electric field is shut off after 8 hours (16 hrs+E (5) versus 8 hrs+E 8 hrs−E (3) or 16 hrs control (4), FIG. 3). These results show that the migration properties of the SCP2 cells are not irreversibly altered by the application of an induced electric field, and that the effects of electrotaxis are reversible once the induced electric field is turned off (8 hrs+E (2) and 8 hrs+E 8 hrs−E (3) versus 16 hrs control (4), FIG. 3).

FIG. 3 illustrates the results showing the effects of turning off the induced electric field on SCP2 cells on the "North" side of the coil after cells have been exposed to it for 8 hours. As indicated in the chart of FIG. 3: 8 hrs control (1): Control experiments used for normalization, showing cells migrated in 0.1% serum media after 8 hours with no induced E field, as 100%. 8 hrs+E (2): Hindered migration (consistent with FIG. 2f) of SCP2 cells in the presence of an induced E field (8 hrs control (1) and 8 hrs+E (2): p<0.001). 8 hrs+E 8 hrs−E (3): Migration of cells after 16 hours, with the induced E field for the first eight hours and the field shut off for the next 8 hours (8 hrs control (1) and 8 hrs+E 8 hrs−E (3): p<0.001). 16 hrs control (4): Control experiments showing cell migration after 16 hours with no induced E field. In this embodiment, cell migration appears to be restored to normal levels despite hindered migration of SCP2 cells due to the induced E field for the first 8 hours (8 hrs+E 8 hrs−E (3) and 16 hrs control (4): p=0.342). 16 hrs+E (5): Migration of cells after 16 hours in the presence of an induced E field (16 hrs control (4) and 16 hrs+E (5): p<0.001).

Weak a.c. electric fields hinder chemotaxis of metastatic breast cancer cells. Experiments on combined chemotaxis and electrotaxis were also performed with the SCP2 cells on the modified trans-membrane assay in order to examine the effects of the induced a.c. electric field in hindering chemotaxis. Two well-known chemokines/growth factors to which SCP2 cells respond, stromal-derived factor 1-α (SDF-1α), also known as CXCL12, and epidermal growth factor (EGF), were selected for investigation and placed in the bottom compartment of the custom-made chamber of the modified transmembrane assay. CXCR4 is a receptor that is overexpressed in malignant breast cancer, and is known to bind to its cognate ligand CXCL12 (SDF-1α) and has been correlated with poor prognosis. EGF is known to be a growth factor that causes leading edge protrusions, an early event in migration of breast cancer cells. CXCR4 positive breast cancer cells have been shown to metastasize to CXCL12 expressing organs as their first destination. It has also been reported that CXCL12/CXCR4 signaling induces actin polymerization and chemotactic property of breast cancer cells. Both SDF-1α and EGF are also well known to initiate chemotaxis of breast cancer cells in the transmembrane migration assay. In these experiments, the induced a.c. electric field was produced by applying the same 20 Vpp, 100 kHz sawtooth shaped voltage waveform described earlier (FIG. 2a).

Figure 4:
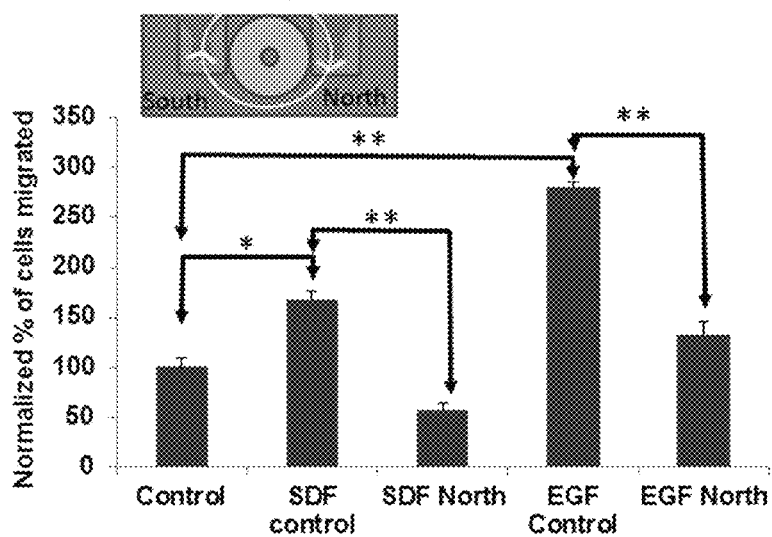
FIG. 4 illustrates the summary of results of SCP2 cell migration in a modified transmembrane assay showing the effects of induced E fields with and without chemokines/growth factors.

Using the system and methods of the present invention, it was determined that even in the presence of chemokines/growth factors such as SDF-1α and EGF, the induced electric fields on the "North" side hinder migration of SCP2 cells relative to migration levels without the field (SDF control versus SDF North, p=0.001; and EGF control versus EGF North, p=0.001, FIG. 4). Chemotaxis control experiments were also performed separately with chemokine SDF-1a (Control ver-sus SDF control, FIG. 4, p=0.015) and growth factor EGF (Control versus EGF control, FIG. 4, p=0.001). Several key observations are immediately evident from these results (FIG. 4). First, chemotaxis is well enabled in the presence of chemokine SDF-1α and growth factor EGF in the modified transmembrane assay. Second, even in the presence of this chemokine and growth factor, the weak induced electric field applied in the direction of migration successfully hinders the migration of SCP2 cells compared to the corresponding cases of chemotaxis in the presence of SDF-1α or EGF alone. This is a significant result since recent works have shown that disruption of the SDF-1α signaling pathway can prevent metastasis and improve the ability of other treatment modalities (radiation or chemotherapy) to attack the tumor.

FIG. 4 illustrates the summary of results of SCP2 cell migration in a modified transmembrane assay showing the effects of induced E fields with and without chemokines/growth factors (SDF-1α or EGF) after 8 hours (N=3). Inset shows schematic end view of apparatus showing the direction of the induced field for ~60% of the 10 µs period. In this embodiment, the function generator drives the coil with a 20 Vpp sawtooth shaped voltage transient at 100 kHz duty cycle. Control: Control without induced E fields or chemokines/growth factors in the modified transmembrane assay. SDF control: Control in the modified transmembrane assay with a Transwell insert, without induced E fields but in the presence of chemokine SDF-1α in the lower chamber (Control vs. SDF control: p=0.015). SDF North: Migration is hindered on the "North" side of the coil, where for the majority (60%) of the 10 µs period, the induced E field is in the direction of migration (i.e., directed downward), even in the presence of the chemokine SDF-1α (SDF control vs. SDF North: p=0.001). EGF control: Control in the modified transmembrane assay with a Transwell insert, without induced E fields but in the presence of growth factor EGF in the lower chamber (Control vs. EGF control: p=0.001). EGF North: Migration is hindered (relative to the case where there is no E field) on the "North" side of the coil, where for the majority (60%) of the 10 µs period, the induced E field is in the direction of migration (i.e., directed downward), in the presence of growth factor EGF (EGF control vs. EGF North: p=0.001).

Figure 5A:
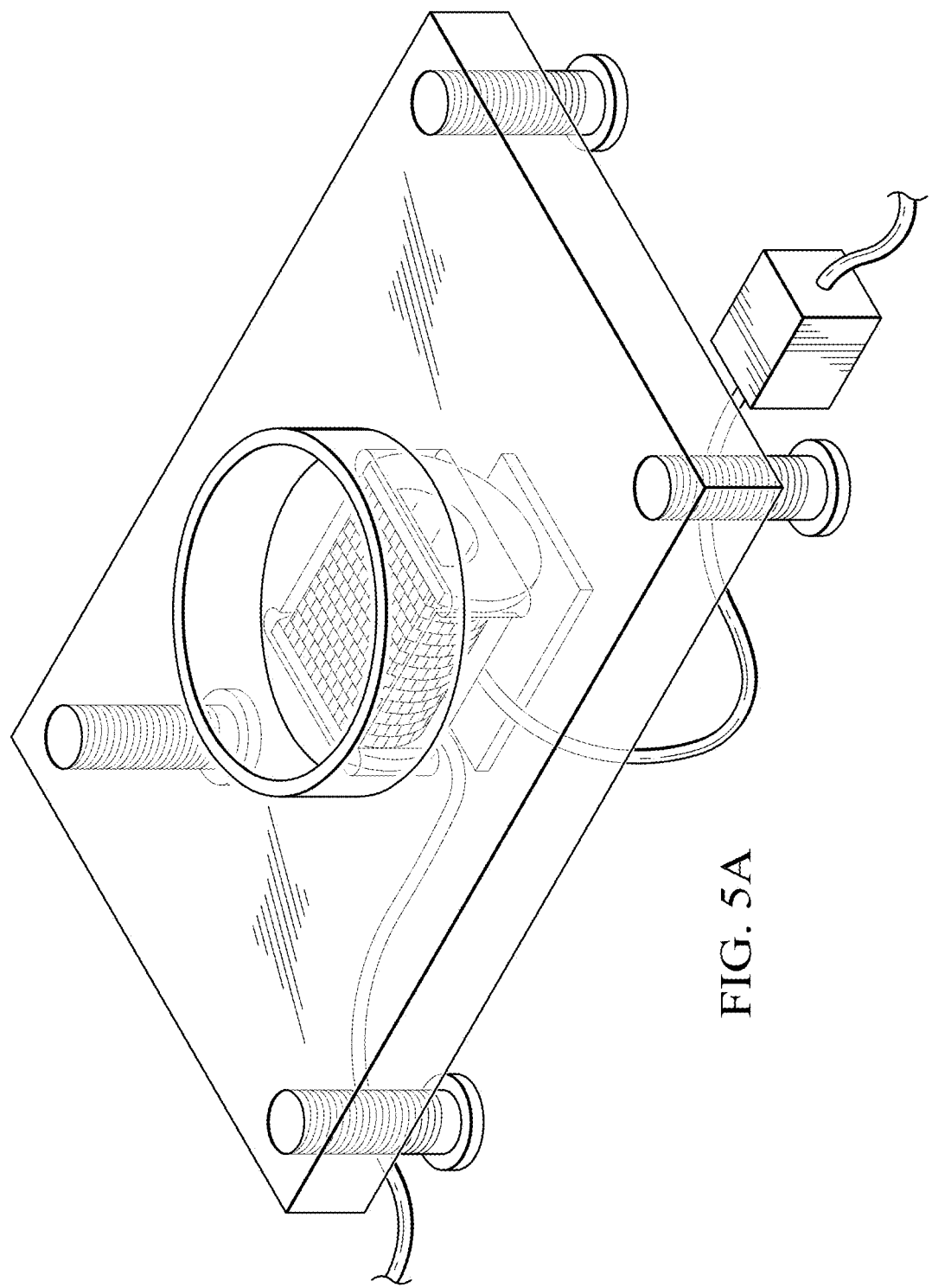
FIG. 5a illustrates one embodiment of an apparatus for visualizing actin filaments under induced electric fields and results of experiments.
Figure 5B:
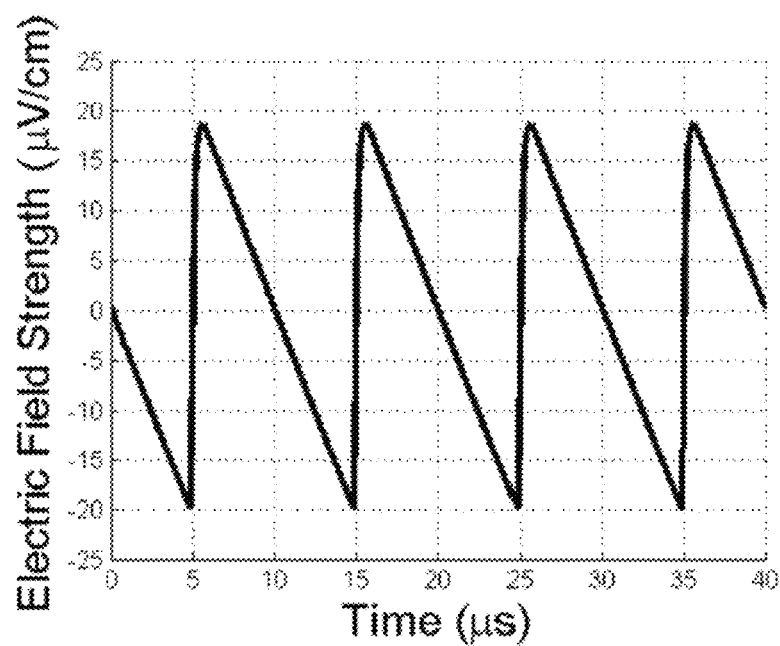
FIG. 5b illustrates the induced electric field versus time showing shape of the field in 10 μs intervals.
Figure 5C:
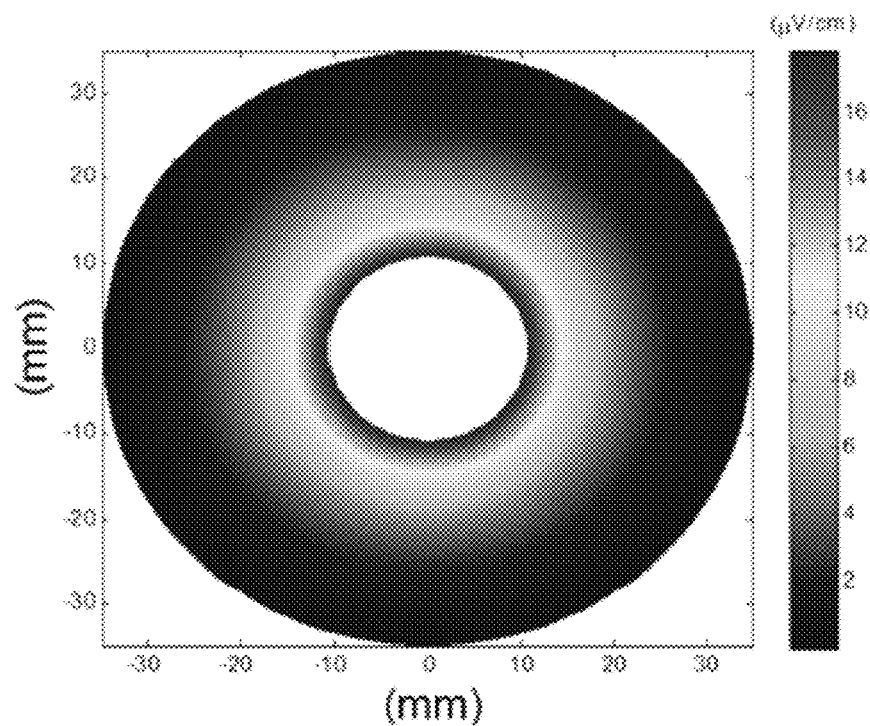
FIG. 5c illustrates contours of induced electric field when viewed from one end of the coil at the instant when the maximum induced E field is ~20 μV/cm.
Figure 5D:
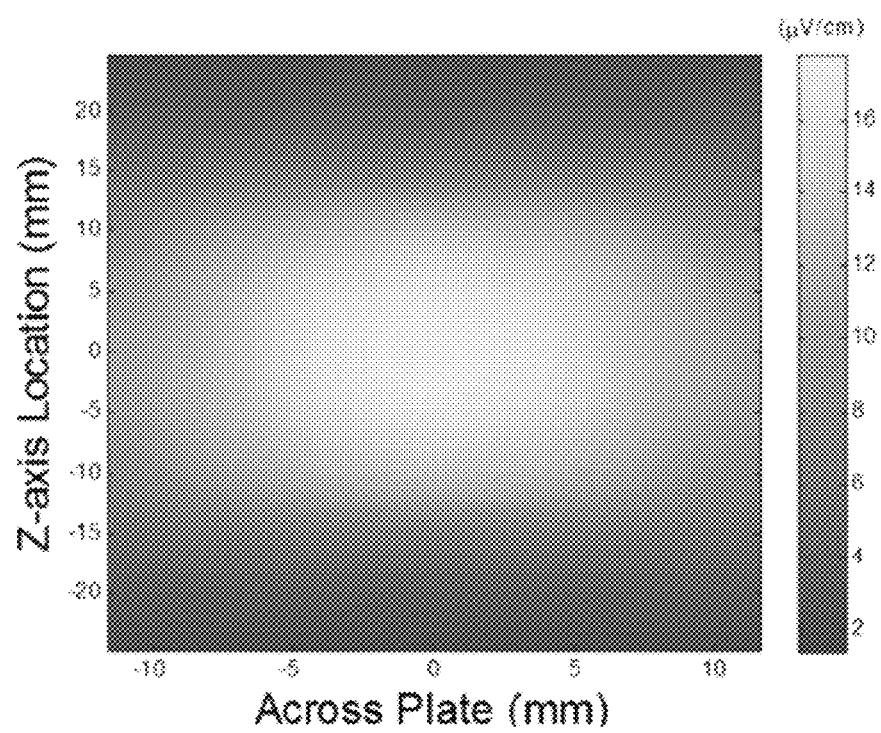
FIG. 5d illustrates a contour plot of the induced E field at the bottom of the culture plate, at the instant when its maximum value is ~20 μV/cm.
Figure 5E:
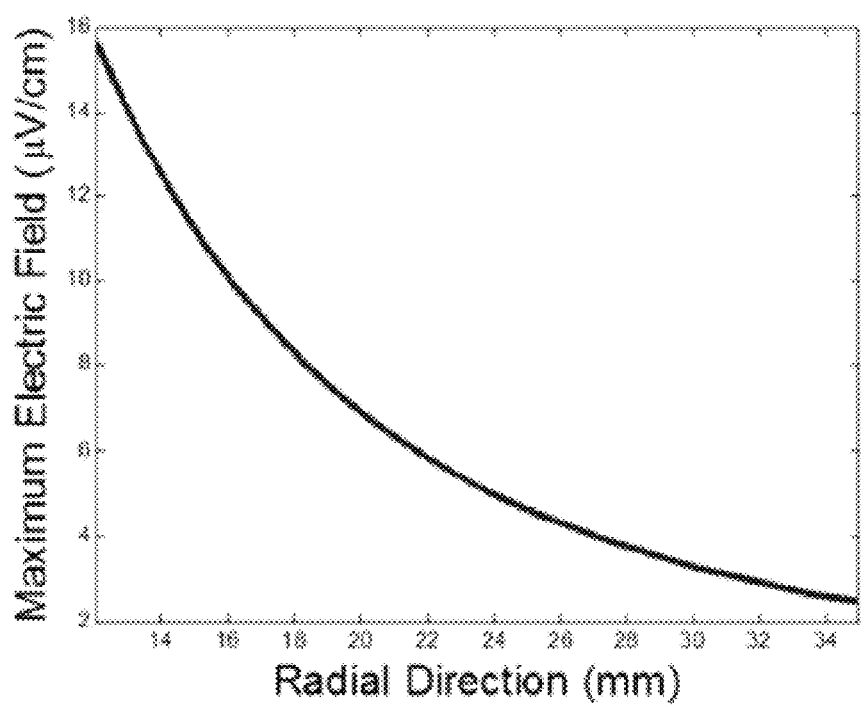
FIG. 5e illustrates the variation of the induced E field versus (radial) distance away from the coil for one embodiment of the invention.
Figure 11:
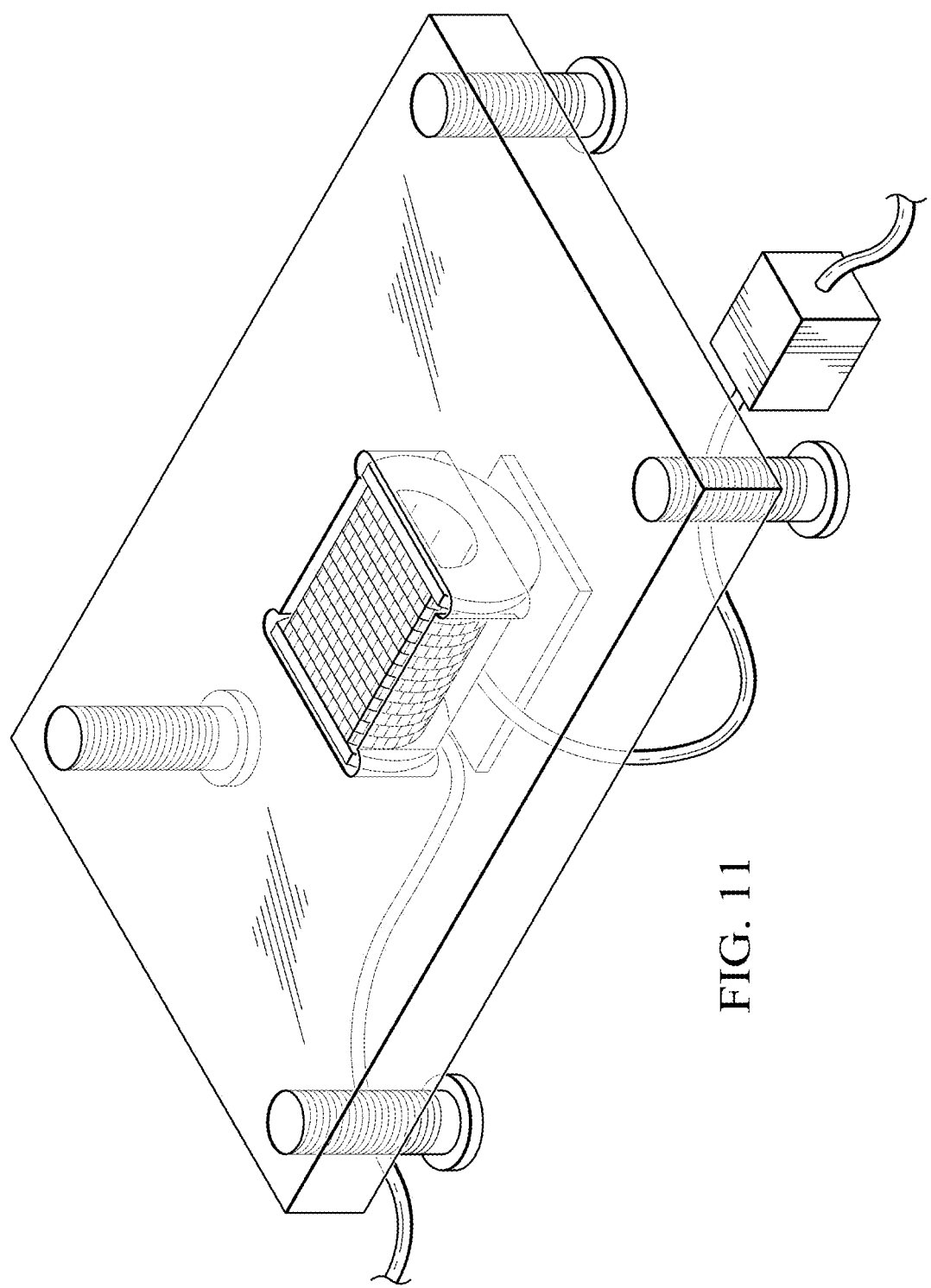
FIG. 11 illustrates one embodiment of a modified holder, coil, and culture plate used in the experiments to image actin filaments using phalloidin and fluorescence microscopy.
Figure 12:
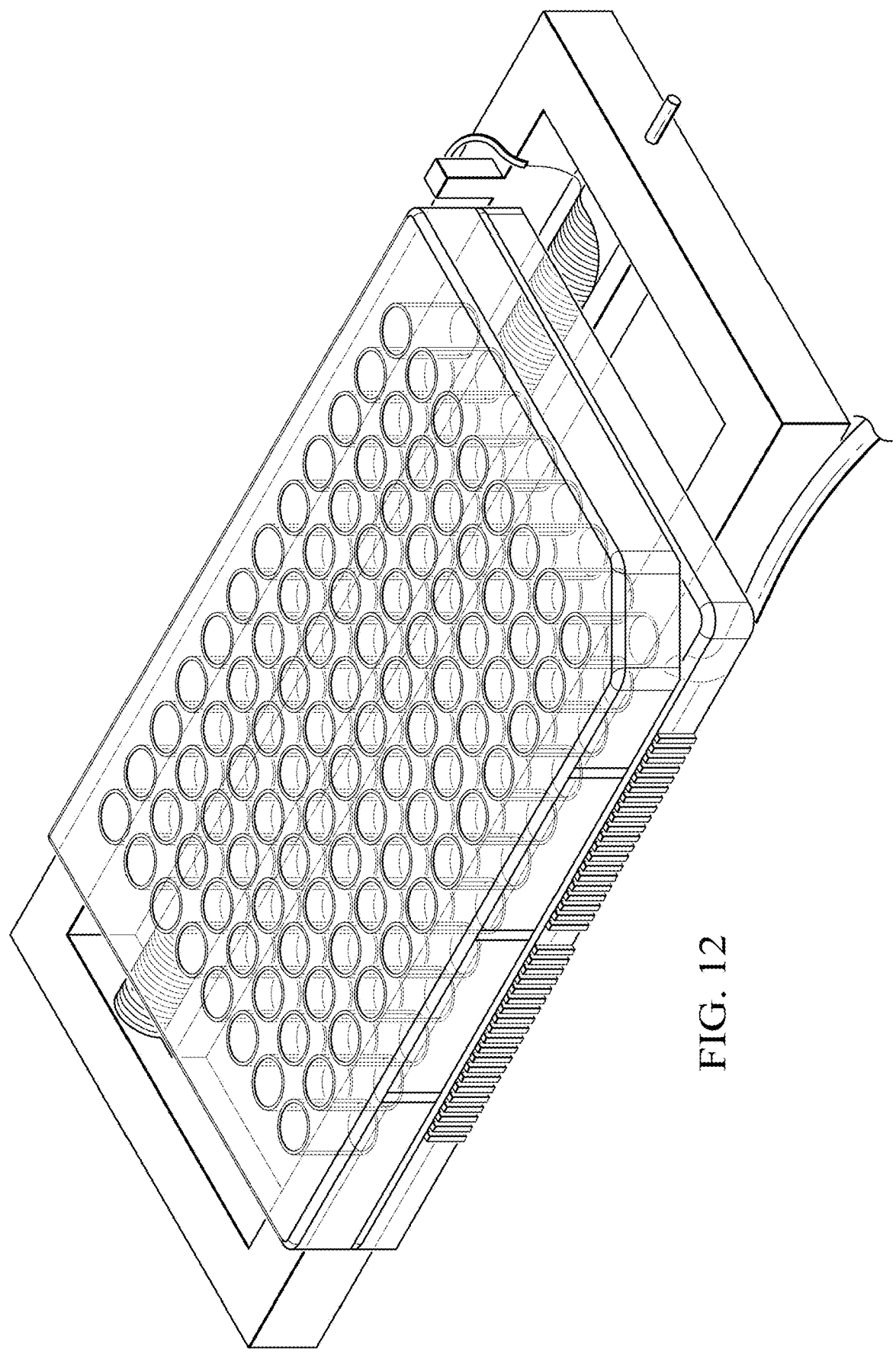
FIG. 12 illustrates one embodiment of how a modified assembly for accommodating a culture plate may be altered for a 96 well multi-well plate.

The apparatus of the present invention enables visualization of actin filaments under induced electric fields. The actin cytoskeleton is known to play an important role in cell migration, especially in transmitting force through adhesion complexes to the substrate. Visualization of actin filaments can therefore help identify so called leader cells and expose any effects of induced electric fields on the internal cell machinery involved in migration. In aid of observing the actin cytoskeleton, a separate holder assembly (FIG. 5a, FIG. 11) can be constructed to orient an electromagnetic coil in such a way as to place a single-well culture plate or a multi-well culture plate on top of a horizontal coil (FIG. 12). In such a configuration, the induced electric field can be calculated for the 20 Vpp, 100 kHz saw-tooth shaped voltage waveform discussed here (FIGS. 5b-5d). Depending on the coil diameter, shape and size, the field can be made uniform over a desired region of the culture plate. This method is particularly well suited to being used in conjunction with the scratch assay.

Figure 18A:
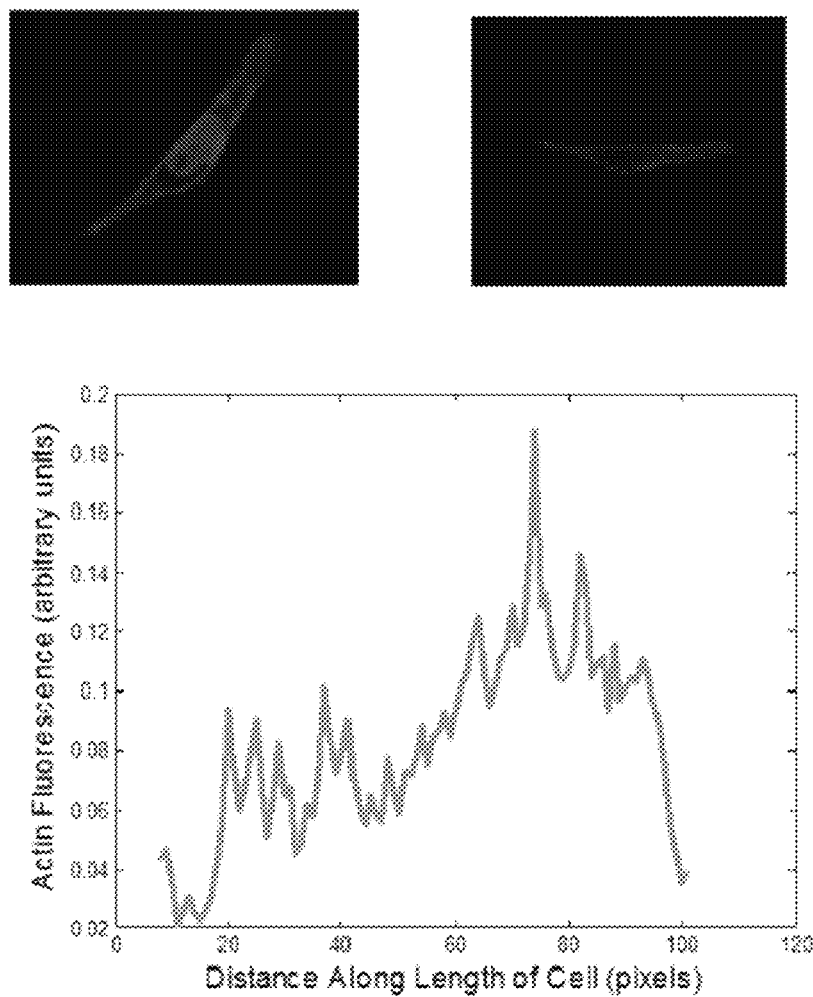
Figure 18B:
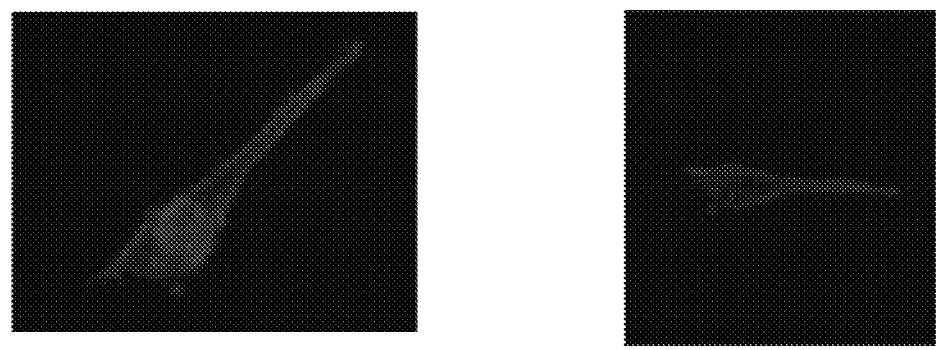
Figure 18B:
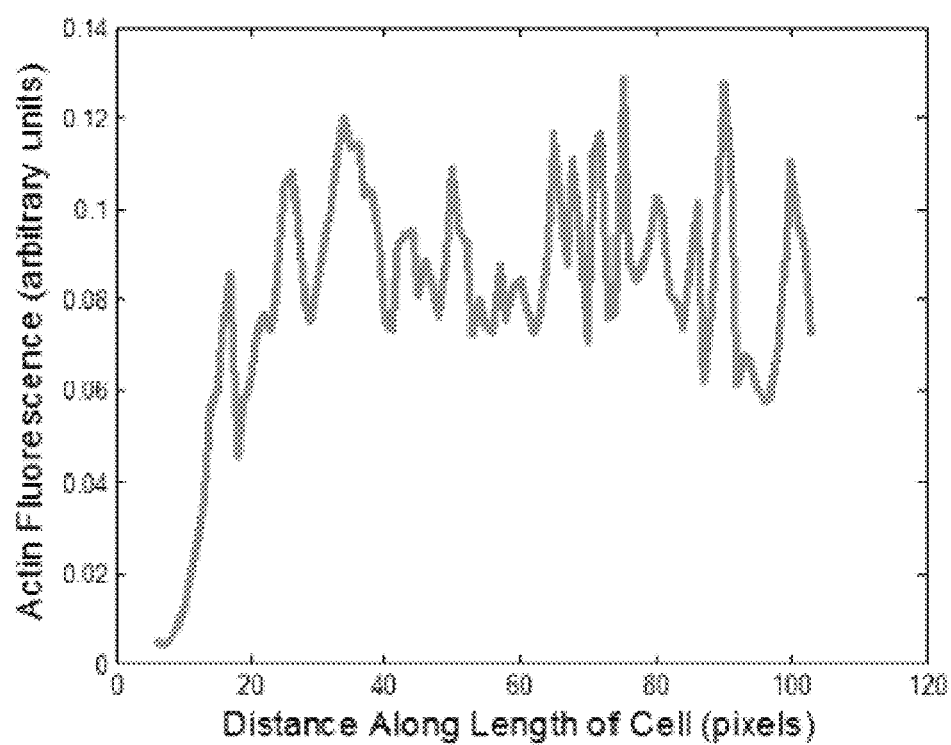
Figure 19A:
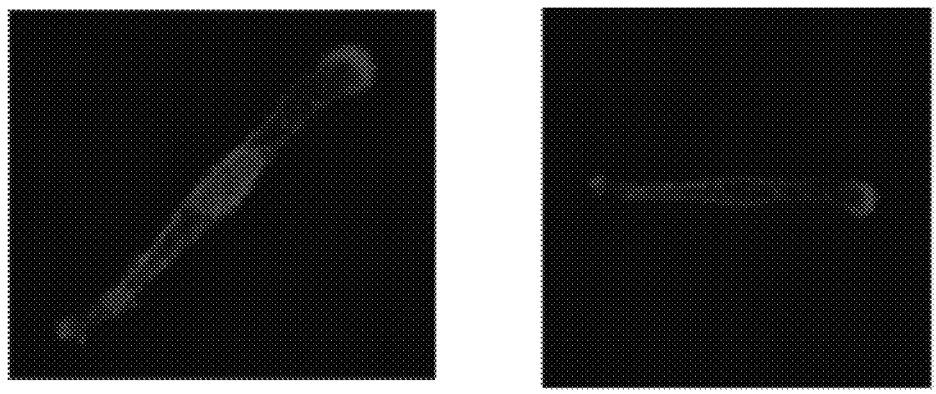
Figure 19A:
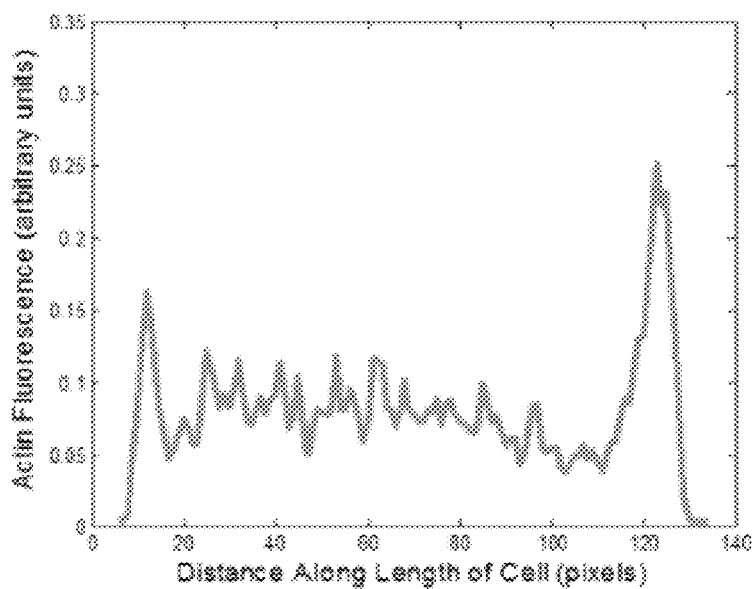
Figure 19B:
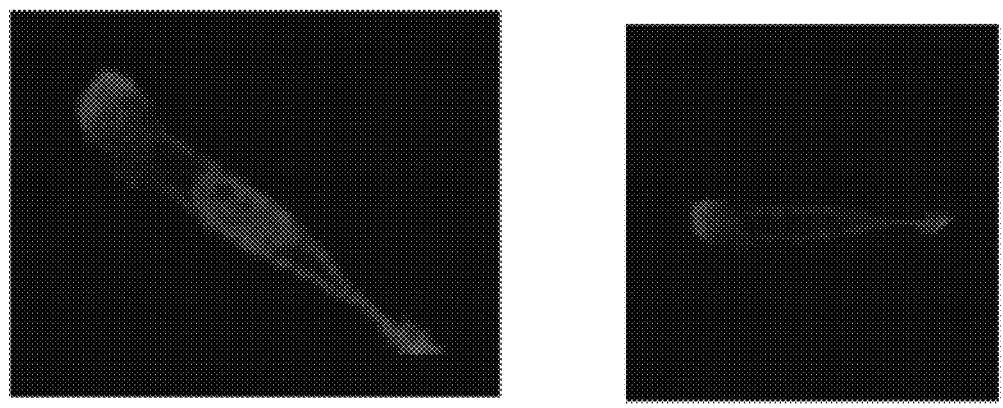
Figure 19B:
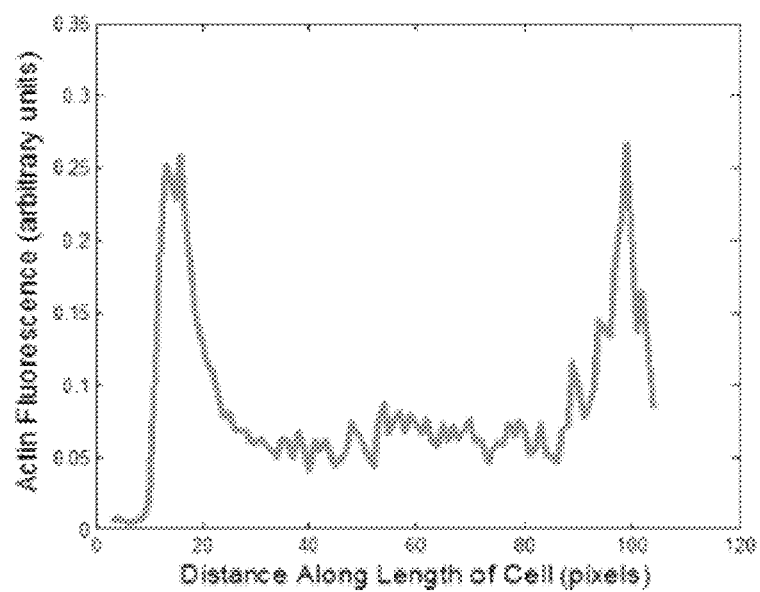

The present invention allows the visualization of actin filaments that form the cytoskeleton of the SCP2 cells and play a crucial role in cell migration, when induced electric fields are applied in a non-contact manner as described earlier (FIG. 6). The images are quantified to determine the actin filament distribution within the cell as represented by the fluorescence intensity. In one embodiment, SCP2 cells are plated on a single-well, 60 mm diameter culture plate, allowed to migrate freely for an hour, and then fixed and stained with phalloidin-fluorophore conjugate for visualization of the actin filaments (FIG. 6a, left panel). SCP2 cells were incubated with EGF for one hour in the presence and absence of induced electric fields and the actin filaments stained with phalloidin-fluorophore conjugate were visualized by confocal microscopy (FIG. 6a, middle and right panels). These images have also been quantified after importing into MATLAB (FIGS. 18-20). In the control case (no electric field and no chemokine), there is little visible polymerization of actin filaments and no discernible preferential direction of formation of filopodia (FIG. 6a left panel, FIG. 18a-b). In contrast, in the presence of the growth factor EGF, polymerization of actin filaments can be observed at one end of some cells (FIG. 6a middle panel, FIG. 19a-b). When an electric field is induced in the presence of EGF, actin polymerization can be seen throughout the cells with no preferential direction and which inhibits formation of filopodia (FIG. 6a right panel, FIGS. 20a-20c). These effects are also apparent when a contiguous layer of SCP2 cells is formed (FIG. 6b). The so-called "leader" cells at the edge of the contiguous layer can be seen to respond to the growth factor EGF (FIG. 6b, left), while in the presence of both EGF and the induced electric field, no directional polymerization of actin is evident (FIG. 6b, right panel).

FIG. 5 illustrates one embodiment of an apparatus for visualizing actin filaments under induced electric fields and results of experiments. In this embodiment, the current through the coil is driven by a 20 Vpp sawtooth shaped voltage waveform at 100 kHz duty cycle. The apparatus is shown with the coil used in actin imaging experiments, in a 3-D printed holder and placed underneath a culture plate. FIG. 5b illustrates the induced electric field versus time showing shape of the field in 10 µs intervals. Note that this coil design yields maximum electric field strengths of ~20 µV/cm, and is approximately symmetric within the 10 µs period (i.e. on for equal duration leftward and rightward). FIG. 5c illustrates contours of induced electric field when viewed from one end of the coil at the instant when the maximum induced E field is ~20 µV/cm. FIG. 5d illustrates a contour plot of the induced E field at the bottom of the culture plate, at the instant when its maximum value is ~20 µV/cm. Note that the induced E field is fairly uniform spatially over a region approximately 1 cm×1 cm. Cells are typically plated in the center of the plate. FIG. 5e illustrates the variation of the induced E field versus (radial) distance away from the coil, at the instant where its maximum value is ~20 µV/cm. Since the thickness of the bottom of culture plates is typically ~1 mm, it is important to keep this variation in mind as one designs coils to exert a particular value of the induced E field at specific locations of a culture plate.

FIG. 6 illustrates the visualization of actin filaments by fluorescence microscopy. FIG. 6a (left panel) actin cytoskeleton in SCP2 cells in the absence of both EGF and induced electric fields. FIG. 6a (center panel) actin cytoskeleton in SCP2 cells in the presence of the growth factor EGF. The white arrows indicate regions of polymerization of actin filaments signifying cellular movement or preparation for movement in response to the growth factor. FIG. 6a (right panel) actin cytoskeleton in SCP2 cells in the presence of EGF and an induced electric field. Note the polymerization of actin filaments within the cell filopodia in the center panel (indicated by white arrows) which are absent in the left and right panels. In the presence of the induced electric field, there is no preferential direction in the formation of the actin bundles.

FIG. 6b (left panel) illustrates the edge of a contiguous layer of SCP2 cells in the presence of EGF, showing actin polymerization (indicated by white arrows) in some cells (so called "leader" cells) as they migrate or prepare to migrate. FIG. 6b (right panel) illustrates the edge of a contiguous layer of SCP2 cells in the presence of EGF and induced electric fields. Note there is no preferential direction for formation of actin bundles. Green and red represent F-actin and nucleus staining, respectively, where the F-actin is detected phalloidin-fluorphore (Alexa Fluor 568) conjugate.

Weak a.c. electric fields hinder chemotaxis of "normal" breast epithelial cells. Experiments on combined chemotaxis and electrotaxis were performed with MCF10A cells in the same modified transmembrane assay in order to examine the effects of the induced a.c. electric field in hindering chemotaxis of non-transformed cells. MCF-10A cells are a non-transformed epithelial cell line derived from human fibrocystic mammary tissue. These cells are considered "normal" breast epithelial cells as they have a karyotype that is nearly diploid, are dependent on externally supplied growth factors for migration, and lack the ability to form tumors in nude mice. The growth factor EGF was used as an exogenous agent to induce MCF-10A cells to migrate in the modified transmembrane assay, as in the case of the SCP2 cells. No migration of MCF-10A cells was observed without EGF in the bottom chamber. As in the previous experiments with SCP2 cells, the induced a.c. electric field was produced by applying the same 20 Vpp, 100 kHz sawtooth shaped voltage waveform (FIG. 2a). Results with the induced electric field and in the presence of EGF were then compared to those of the control cases in the presence of EGF and no induced electric field.

Figure 22:
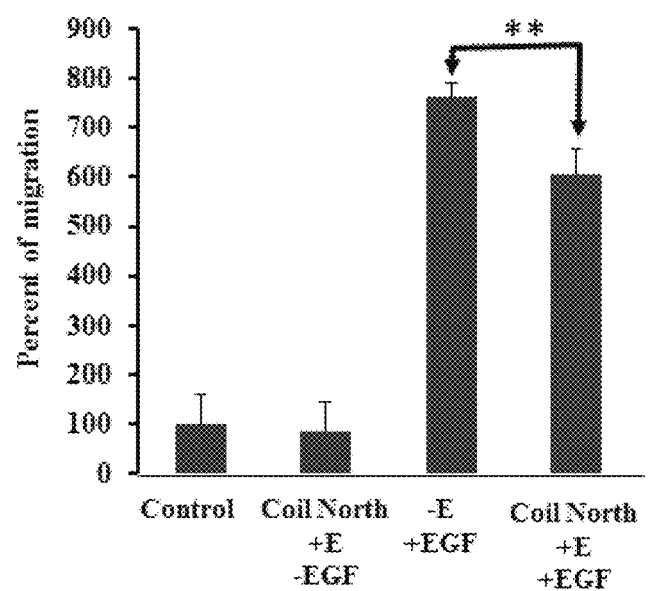
FIG. 22 illustrates a chart showing a summary of experimental results of migration of MCF-10A cells in the modified transmembrane assay showing the effects of induced electric fields with and without the growth factor EGF.

The experimental results with the MCF-10A cells are summarized in FIGS. S15-S16. It can be seen that the MCF-10A cells do not migrate without the presence of the growth factor EGF. Furthermore, the induced electric fields on the "North" side hinder migration of MCF-10A cells relative to migration levels without the field in the presence of EGF (Coil North+E+EGF (4) versus–E+EGF (3), p=0.002; FIG. 22). In contrast, induced electric fields on the "South" side do not affect MCF-10A cell migration in a statistically significant manner (data not shown).

Figure 1B:
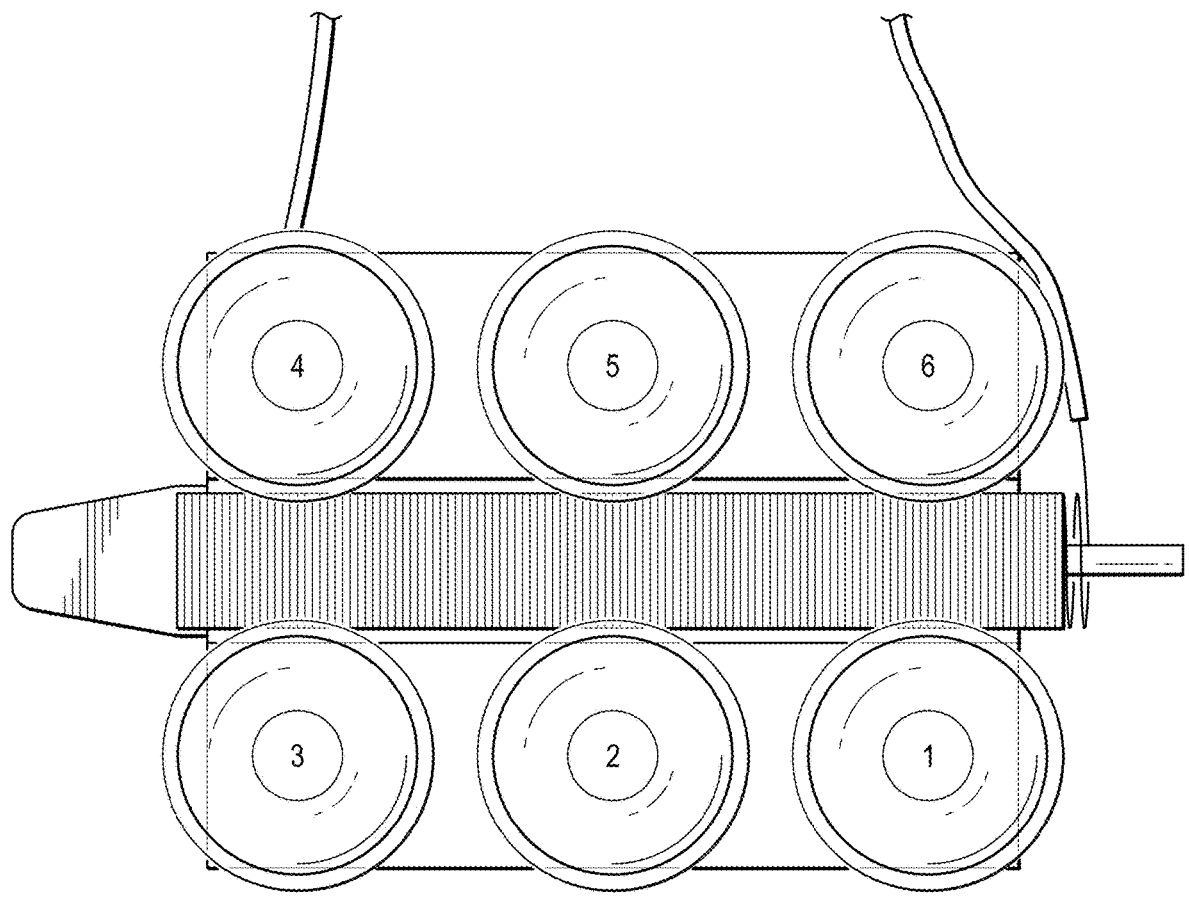
FIG. 1b illustrates a top view of a modified transmembrane assay.

The present invention includes a method for inducing electric fields by electromagnetic induction (according to Faraday's Law) and driving electrotaxis without the need for electrodes in contact with the media containing cell cultures. This method has been applied and demonstrated on the modified transmembrane assay commonly used for studying chemotaxis. The modification to the existing transmembrane assay consists of glass wells (FIG. 1, FIG. 7) that are designed to incorporate commercially available membrane inserts, placed on either side of an in-house designed and fabricated coil (FIG. 1a), and placed on a holder that is fabricated using 3-D printing technology (FIG. S2). The method can be applied to other cell migration assays such as the scratch assay. By changing the length and diameter of the coil and associated holder, the method is also compatible with commercially available multi-well culture plates (FIG. S6).

Experiments in the modified transmembrane assay using a single cell population SCP2 isolated from the MDA-MB-231 breast cancer cell line show that application of weak induced electric fields (on the order of ~1 µV/cm) is able to mitigate normal migration of these cells when the electric field is applied in the direction of migration. Moreover, SCP2 cell migration is also hindered in the presence of these weak a.c. induced electric fields, in the presence of the well-known chemokine SDF-1α and growth factor EGF. This is the first time that such low-level electric fields (as low as six orders of magnitude smaller than previously reported) have been shown to have an effect on electrotaxis. No negative effects of the induced electric fields on the cells have been observed. In fact, experiments in which the induced electric field was applied for 8 hours to hinder SCP2 cell migration revealed that the cells continued to migrate normally when the electric field was shut off.

Experiments have also been performed on the non-transformed human mammary epithelial cells MCF-10A in the modified transmembrane assay. These cells do not normally migrate unless growth factors are externally supplied. Results from these experiments also show that application of weak induced electric fields is able to hinder their migration in the presence of growth factor EGF and when the field is applied in the direction of migration. These experiments show that the platform for applying induced electric fields presented here is applicable to different cell lines, both non-transformed and transformed. The usefulness of the present method may extend beyond using the modified trans-membrane assay for quantifying the degree of metastasis of a particular cell line, or for studying electrotaxis when subjected to an a.c. field in a non-contact manner and in the presence of chemokines. The non-contact manner in which the E-field is applied may be useful in inhibiting metastasis, or in orchestrating wound healing in vivo. By varying the direction and spatial extent of the induced electric field, the approach presented here can enable different cells (e.g. keratinocytes, fibroblasts, endothelial cells, and macrophages) to migrate at different times during the wound healing process resulting in accelerated healing beyond just the superficial layers. Application of electric fields over periods of hours and days is also physiologically relevant in the treatment of cancers. So called tumor treating fields (TTF) have been successfully used to treat recurrent glioblastoma (GBM) and extend patient survival. While the mechanism of action of TTFs may be different than the method presented here (the induced a.c. electric fields in this work are up to six orders of magnitude smaller), cell migration may be affected in both approaches. By combining the ability to simultaneously study chemotaxis and electrotaxis using the modified transmembrane assay, new combinations of treatment strategies and drugs may be identified or ruled out earlier in the drug discovery screening process by revealing undesirable effects.

Figure 7:
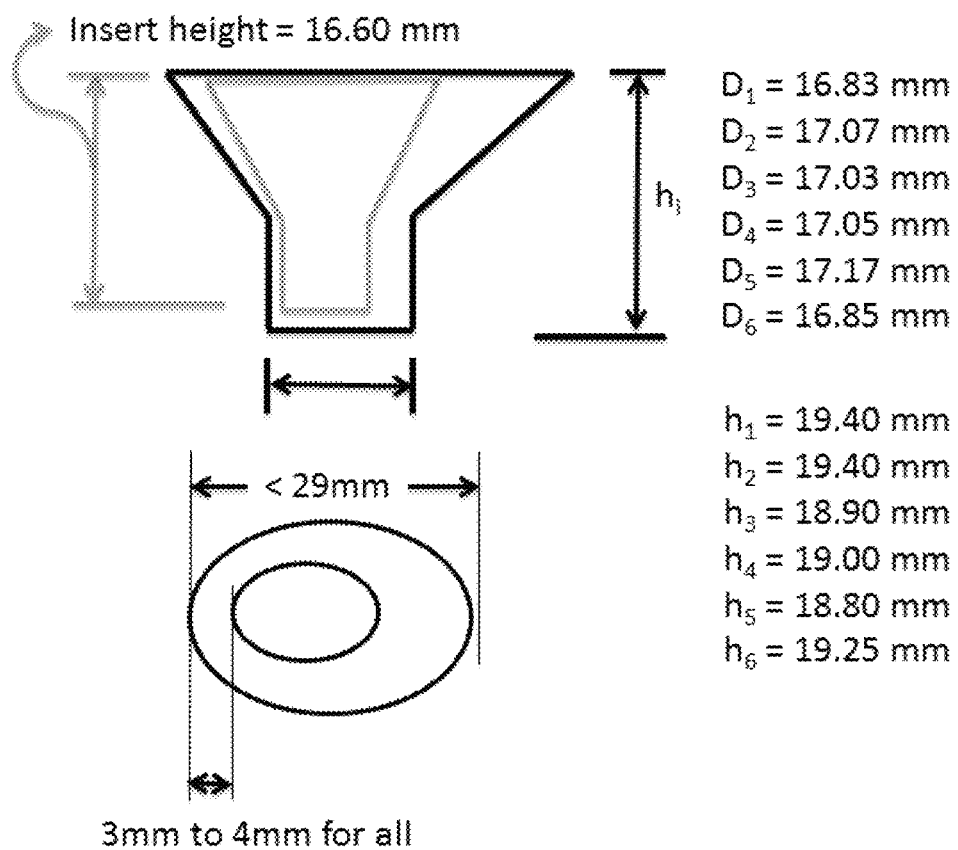
FIG. 7 illustrates one embodiment of a side-view of a glass well depicting inserts.
Figure 8:
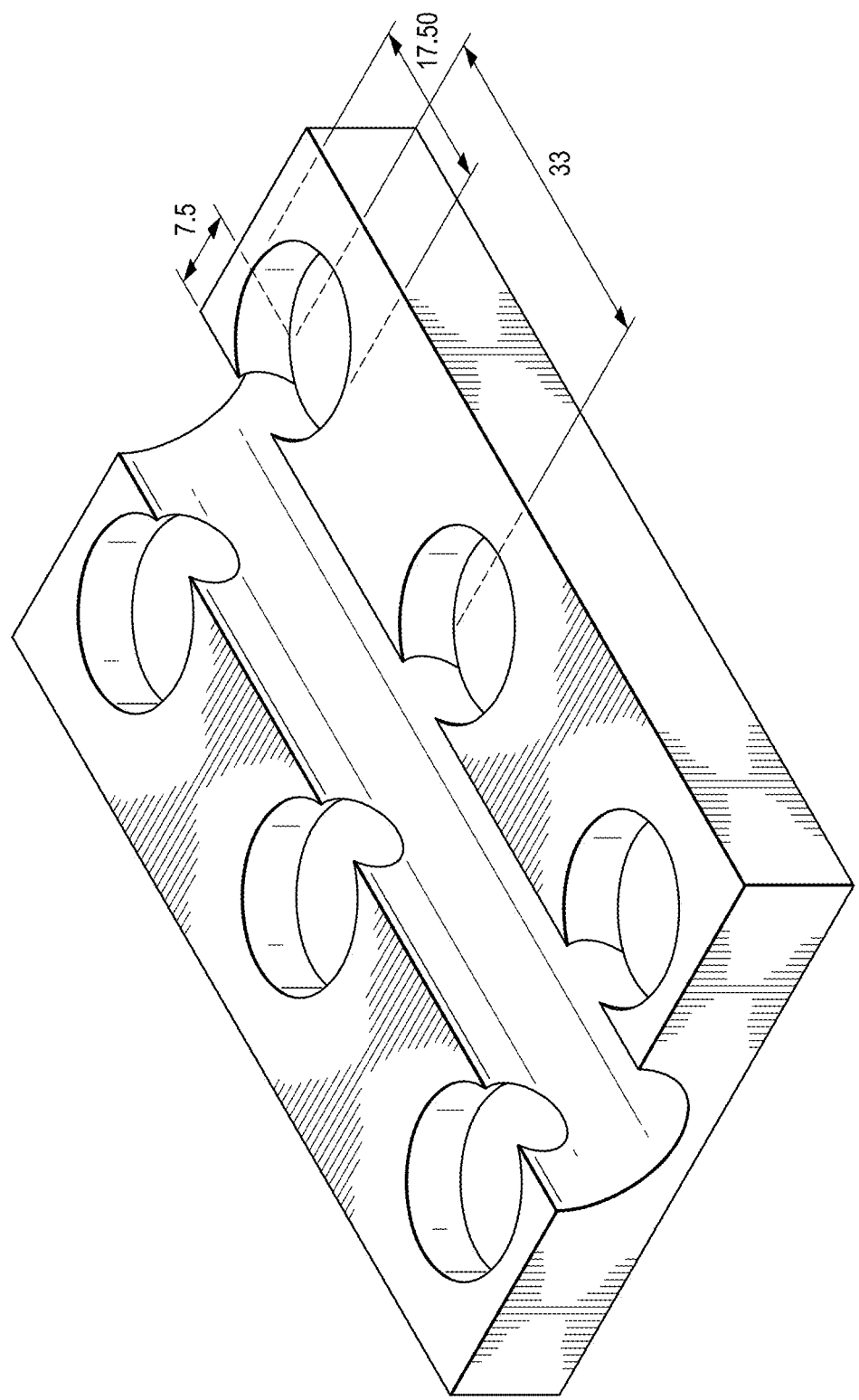
FIG. 8 illustrates one embodiment of a holder of the present invention.

In one embodiment, the custom made glass wells are only identical in dimension up to fractions of a millimeter (FIG. 7). Consequently, the holder is preferably designed using computer-aided design (CAD) methods and fabricated after the glass wells have been made. Once the dimensions of the glass wells have been determined (FIG. 7), a CAD drawing is developed using the commercially available software SolidWorks (FIG. 8). The holder is then printed using plastic material according to the specifications on the CAD drawing on a 3D printer (Stratasys Fortus 400 MC). Since the outer radius of the coil may vary along its length due to unevenness of the windings, it is recommended that the middle channel where the coil is to reside be made of the smallest outer diameter of the coil so that specific locations in the channel may be ground manually to ensure that the coil fits in the center channel properly. The depth of each well in the holder is designed so as to ensure that the membrane is positioned exactly at the height corresponding to the centerline of the coil (FIGS. 1b-1e).

Fabrication of the coil for the modified transmembrane assay experiments: The electromagnetic coil used to generate the induced electric fields across the transmembrane inserts is comprised of multiple windings (35 layers, ~159 turns per layer) of insulated 32 AWG (0.268 mm diameter with insulation or 0.202 mm diameter bare) wire wound around a glass rod. The inner diameter of the coil is 3 mm, the outer diameter is 1.4 cm, and its length is 10.5 cm. The coil resistance and inductance were measured using an LCR meter (Extech Instruments Model 380193) to be 50.45$\Omega$ and 14.25 mH, respectively, at 1 kHz. The coil is placed at the center of the holder (FIG. 8) with six glass wells on either side. The wire gage, inner and outer diameters, number of turns, length, and number of layers in the coil can be varied depending on the type of experiment to be conducted. The duty cycle of the imposed voltage (which is 100 kHz for the results presented here) and its magnitude can also be easily changed. It is important to ensure that the function generator (Hewlett Packard 33120A 15 MHz in the present experiments) is able to drive sufficient current through the coil.

Fabrication of custom glass wells to accommodate transmembrane inserts, analysis of induced electric fields in modified transmembrane assay experiments, analysis of induced electric fields in visualization of actin filaments, and supple-mental data on migration of MCF-10A cells with and without growth factor EGF and with and without induced electric fields, are described in more detail below.

In one embodiment, low passage SCP2 cells were cultured in Dulbecco's Modified Eagle's Media (DMEM) containing 10% fetal bovine serum (FBS) and 5 U/mL penicillin, and 5 mg/mL streptomycin at 37° C. in a humidified culture incubator supplied with 5% $CO_2$. To perform cell migration and actin filament imaging experiments, SCP2 cells were washed with serum free media three times and incubated with 0.1% FBS-DMEM media for six hours. The cells were detached from the culture plates by incubating in 1 mL of trypsin-EDTA for 2-4 min. The trypsin was neutralized by adding 2 mL of 0.1% FBS-DMEM. The cells were centrifuged at 1200 rpm for five minutes and re-suspended in 1 mL of 0.1% FBS-DMEM. The cells were counted using a hemocytometer. $1.5 \times 10^5$ cells in 150 µL of media were placed in the top chamber of the modified transmembrane assay. The bottom chamber was filled with 600 µL of 0.1% FBS-DMEM with or without 100 ng/mL of chemokine (SDF-1$\alpha$) or growth factor (EGF). After allowing 8 or 16 hours of incubation in the modified transmembrane assay, the cells that migrated to the other side of the Transwell membrane in the top chamber were stained with Hema 3 stain kit (Fisher Scientific, 122-911) according to the manufacturer's instructions. The stained cells were then photographed with a Zeiss microscope attached to a camera. The migrated cells were counted in five representative fields. As an illustration, four representative fields for a control case and a case with the induced electric field are shown in FIG. 9.

In one embodiment, MCF10A cells were cultured in Dulbecco's Modified Eagle's Media (DMEM) F12 containing 5% horse serum (HS), 20 ng/ml epidermal growth factor (EGF), 0.5 mg/ml hydrocortisone, 100 ng/ml cholrea toxin, 10 µg/ml insulin and 5 U/mL penicillin, and 5 mg/mL streptomycin at 37° C. in a humidified culture incubator supplied with 5% $CO_2$. MCF10A cells were prepared for migration assay using 0.1% HS-DMEM-F12 media as described above. $1.5 \times 10^5$ cells in 150 µL of media were placed in the top chamber of the modified transmembrane assay. The bottom chamber was filled with 600 µL of 0.1% HS-DMEM-F12 with or without 50 ng/mL EGF. After allowing migration for 16 hours, cells were stained, photographed and counted as described for the preparation of the SCP2 cells.

For the actin imaging experiments, the SCP2 cells were cultured in 60 mm culture dishes (Falcon, 353001) overnight in 10% FBS-DMEM and subsequently incubated in 0.1% FBS-DMEM for at least six hours. In another experiment to make a contiguous layer of cells, a straight wound (scratch) was created by the tip of 200 µL pipette tip. The simulated wound was aligned on top of the coil axis to observe the effects of the induced electric field on EGF-induced actin polymerization.

The cells were incubated in EGF (100 ng/mL) for one hour in the presence or absence of an induced electric field. Subsequently, the cells were washed with ice cold PBS and fixed with 4% paraformaldehyde. Further, the cells were permeabilized by 0.1% triton X-100 for 15 min and stained with Phalloidin conjugated with the fluorophore Alexa Fluor 568 (1:300×) (Molecular Probes) for one hour. Finally, the cells were mounted with VECTASHIELD hard set mounting media with DAPI (Vector labs) and visualized using an Olympus FV1000 confocal microscope.

To achieve statistical significance, in some cases three independent experiments consisting of three wells each were performed and representative data presented. In other cases, two independent experiments consisting of two wells were performed. The data were computed as mean±SD. Group means were compared by using the Student t test and $p<0.05$ was considered as significant. Statistical analysis was performed with Microsoft excel (Microsoft Corporations, USA). Statistical significance is denoted in the figures by '*' ($0.01 \leq p < 0.05$), '' ($0.001 \leq p < 0.01$), and '*' ($p < 0.001$). Where sample sizes (N) are indicated, these denote results from independent experiments. For example, N=3 refers to three independent experiments measuring migration on for example the "North" and includes the three wells on that side of the coil.

Fabrication of custom glass wells to accommodate transmembrane inserts: in one embodiment, the glass wells (FIG. 1b-e and FIG. 7) in which the transmembrane inserts can be placed were made from 14.6 mm I.D.×17 mm O.D. borosilicate glass tubing (C.O.E. $32 \times 10^{-7}$). Using a fixed carbon roller adjusted to an angle of 120 degrees to the glass tubing as it turned being chucked in a lathe, a hand torch heated the material until a suitable working state of the glass was reached. Air was introduced through the center of the closed end tube, expanding the molten material until it made contact with the graphite roller. The roller shaped the material into the desired conical shape, leaving a tubular opening on each end to be closed later. Following formation of the well shape, the larger end was closed and shaped flat, this surface being perpendicular to the wall of the stock tubing. The finished end was then fixed into the tail chuck of the glass working lathe to allow the part to be temporarily separated from the stock material from which it had been formed. The stock material was closed flat and perpendicular to its wall, leaving only a small opening in the form of a tabulation shape, to allow for expanding air inside the well to escape as the part was sized. The lower portion was finished to measure approximately 9 mm in length from the closed bottom up to the point where its diameter began to expand into the shape of a funnel. Once separated from the stock tubing, and leaving only a small tabulation, the part was annealed in a furnace at 570° C. for 20 minutes, and allowed to naturally cool to room temperature.

The closed top was finished with a 16 mm diameter hole cut close to one side or off center from the center of the part. This allows the transmembrane insert to be placed as close to the inside wall of the glass well (and hence the outer surface of the coil) as possible. For consistency, a wooden block was drilled to accept the glass well lower-diameter feature to a depth large enough to allow clearance for the temporary tabulation. This wooden block was then positioned and clamped onto the stage of a drill press, in a position adjusted to where the outside diameter of the cutter was 2.5 mm off center from the outside wall of the 14.6 mm×17 mm O.D. lower part of the well. Positioned in this manner, the cutter (made of brass) formed a hole off center in the desired position allowing the transmembrane insert to rest against the wall of the lower portion of the glass well. The glass well held in the wooden jig had modeling clay applied to the outside of the rim to contain 100 grit carborundum cutting powder slurry mixed with water. The action of the brass mandrel turning against the flat glass surface of the top of the well with the cutting compound slurry proceeded to grind through over approximately 15 to 20 minutes. A pecking action was employed to reintroduce new cutting compound into the "groove" being formed.

The bottom was permanently closed after cleaning the part to remove the cutting compound and modeling clay. The part was chucked into the glass working lathe from the wider, flared end. As the part turned, it was warmed before a small torch was applied to heat the glass to a suitable working temperature allowing for the temporary tabulation to be removed. The part was then allowed to cool, before being turned in the opposite direction and chucked again into the lathe to apply a final finish on the 16 mm diameter opening on the wider end. Finishing the open, 16 mm diameter end involved bringing the part back to a warmed condition before polishing the ground surface left from grinding the opening with the brass mandrel. Once warmed, a small hand torch was used to fuse the surface of the cut a little at a time until the entire circumference of the opening was "fire" polished. Care was taken not to overheat the surfaces so as to not distort any other part of the well. The part was then flame annealed to a point safe from cracking before finally being oven annealed, as described earlier.

Analysis of induced electric fields in modified transmembrane assay experiments: a time-dependent magnetic induction ($\partial \vec{B}/\partial t$) must be present in order to induce an electric field in a non-contact manner. Such an induced electric field can be produced either by a constant magnitude magnetic field that is changing its direction versus time or by a magnetic field in a specific direction that is changing its magnitude with respect to time, or both. In this embodiment, the latter approach was used.

The 20 Vpp, 100 kHz sawtooth shaped voltage waveform (FIG. 2a) imposed on the electromagnetic coil results in a time-dependent current flow through it. The current through the coil varies in time both in magnitude and direction, and is a complicated function of the inductance and intrinsic capacitance of the coil as well as its coupling with the function generator. Consequently, the resulting magnetic induction in cylindrical coordinates, $\vec{B}(r,z,t)$, and associated vector potential $\vec{A}(r,z,t)$ vary with time both in magnitude and direction, where r and z are the radial and axial coordinates measured from an origin located at one end of the coil along its centerline. The induced electric field $\vec{E}(r,z,t)$ can then be calculated from the vector potential, $\vec{A}(r,z,t)$:

$$\vec{E} = -\frac{\partial \vec{A}}{\partial t} \qquad (1)$$

Figure 13:
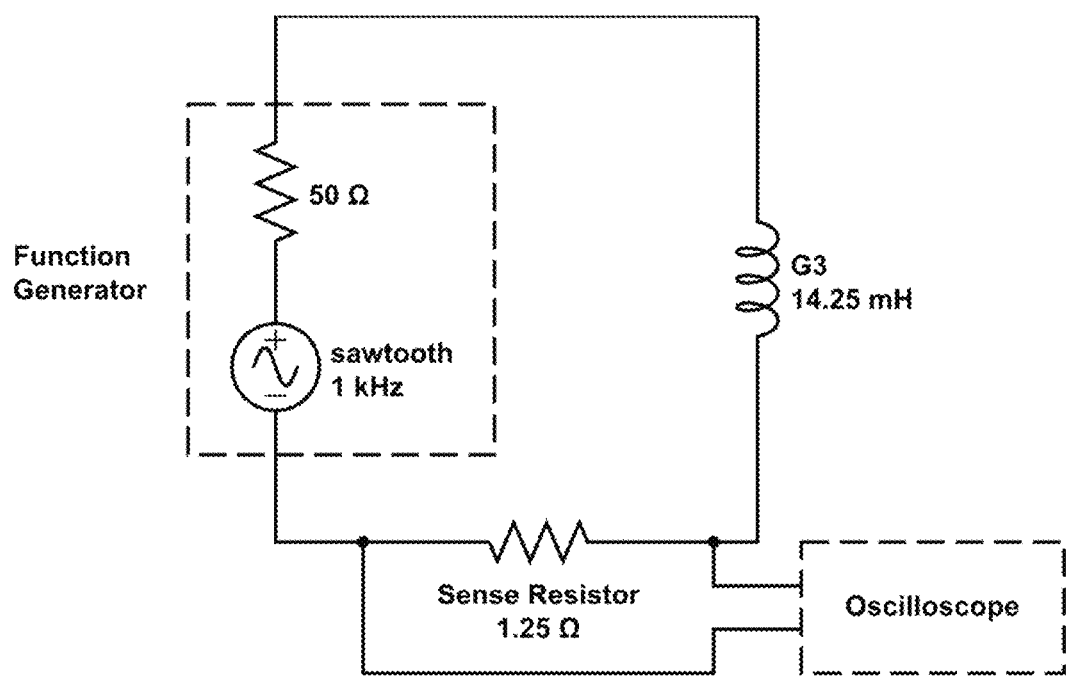
FIG. 13 illustrates one embodiment of a circuit diagram showing the use of a sense resistor to measure the current through the coil.

The time-dependent current through the coil can be measured using a sense resistance (a smaller resistance) connected in series with the coil in the circuit, and by measuring the time-dependent voltage drop across the 1.25 Ω sense resistance (FIG. 13). Extreme care must be taken so as to ensure that no stray capacitances arising for example from BNC connectors corrupt the measurement. One way to verify the measurement, is to connect the sense resistance upstream of the coil and ensure that the same current profile versus time is obtained as when the sense resistance is connected downstream of the coil. It is also important to point out that use of a sense resistance for current measurement is only reliable at low values of the duty cycle (on the order of tens of kHz or lower) because of the unknown intrinsic coil capacitance which is difficult to quantify at high values of the duty cycle (e.g. at 100 kHz) due to leakage.

The following methodology is used for calculating the induced electric fields relevant to the present invention. The current through the electromagnetic coil is measured for an imposed sawtooth voltage waveform of 20 Vpp at 1 kHz using a 1.25Ω sense resistance (FIG. 13). A circuit element model (FIG. 14) is then used to predict the current through the coil at 1 kHz, and validated against the current measurement using the sense resistance at 1 kHz. The model is used to infer the intrinsic coil capacitance (FIG. 14), and then used to predict the coil conduction current for the experimental conditions where the imposed 20 Vpp sawtooth shaped voltage waveform is applied at 100 kHz. Once the time-varying current is calculated, the vector potential $\vec{A}(r,z,t)$ is calculated using an analytical solution for the vector potential at a point given a circular current winding of a given diameter at a specific location:

$$A_{\phi,j} = \frac{\mu_0 I}{\pi} \sqrt{\frac{a_j}{m_j r}} \left[ \left(1 - \frac{m_j}{2}\right) K(m_j) - E(m_j) \right] \qquad (2)$$

where $$m_j = \frac{4a_j r}{[(a_j+r)^2 + (z-l_j)^2]},$$

where $K(m_j)$ is the complete elliptic integral of the first kind, $E(m_j)$ is the complete elliptic integral of the second kind, l is the current through winding j, $a_j$ is the radius of the $j^{th}$ winding, r is the radial coordinate, z is the axial coordinate (with the origin taken along the centerline of the coil and at one end of the coil), and $A_{\phi j}$ is the contribution to the vector potential at (r,z) at time t due to current l(t) flowing in the $j^{th}$ winding. By taking the coil to be comprised of a perfectly stacked set of wire loops (windings) with different diameters and carrying the same current, the vector potential at any point in space can be obtained as the superposition of the individual contributions from each loop of wire in the coil:

$$A_\phi = \sum_{j=1}^{N} \frac{\mu_0 I}{\pi} \sqrt{\frac{a_j}{m_j r}} \left[\left(1 - \frac{m_j}{2}\right) K(m_j) - E(m_j)\right] \quad (3)$$

where N is the total number of windings in the coil (35 layers×159 windings per layer=5565). Note that in Eq. (3) the only time dependent quantity is the current l. The radial and axial components of magnetic induction are then calculated from:

$$B_r = -\frac{\partial A_\phi}{\partial z} = \sum_{j=1}^{N} \frac{\mu_0 I}{2\pi} \frac{(z-l_j)}{r\sqrt{(a_j+r)^2+(z-l_j)^2}} \left[-K(m_j) + \left(\frac{a_j^2 + r^2 + (z-l_j)^2}{(a_j-r)^2 + (z-l_j)^2}\right) E(m_j)\right] \quad (4)$$

$$B_z = \frac{A_\phi}{r} + \frac{\partial A_\phi}{\partial r} = \sum_{j=1}^{N} \frac{\mu_0 I}{2\pi} \frac{1}{r\sqrt{(a_j+r)^2+(z-l_j)^2}} \left[K(m_j) + \left(\frac{a_j^2 - r^2 - (z-l_j)^2}{(a_j-r)^2 + (z-l_j)^2}\right) E(m_j)\right] \quad (5)$$

and the induced electric field is given by:

$$E_\phi = -\frac{\partial A_\phi}{\partial t} = -\frac{\mu_0}{\pi} \left(\frac{dI}{dt}\right) \sum_{j=1}^{N} \sqrt{\frac{a_j}{m_j r}} \left[\left(1 - \frac{m_j}{2}\right) K(m_j) - E(m_j)\right] \quad (6)$$

where $$m_j = \frac{4a_j r}{[(a_j+r)^2 + (z-l_j)^2]}.$$

Note that the induced electric field $E_\phi$ calculated from (6) varies with the radial coordinate r and axial coordinate z. For the case of rapidly changing transients, it is recommended that the derivative dI/dt in equation (6) be calculated using higher order accurate finite difference formulae such as a fourth-order accurate finite difference formula.

Figure 14:
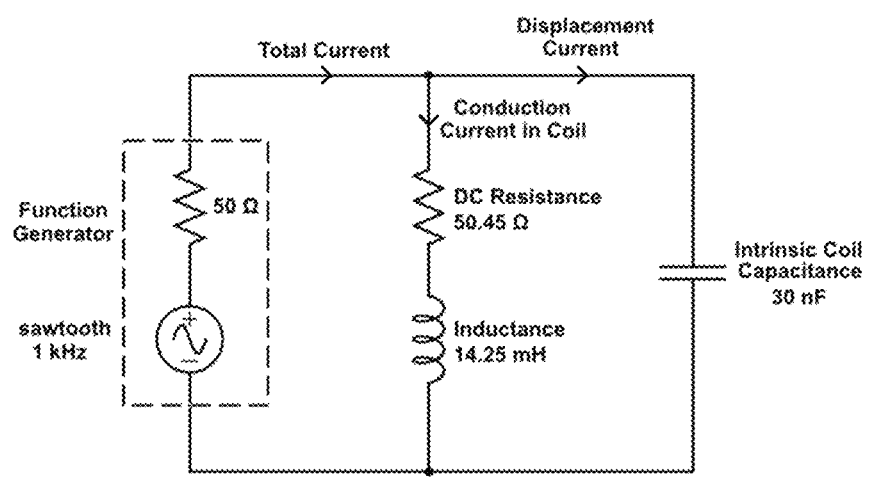
FIG. 14 illustrates one embodiment of a circuit diagram showing a model used to predict the current through the coil.
Figure 15:
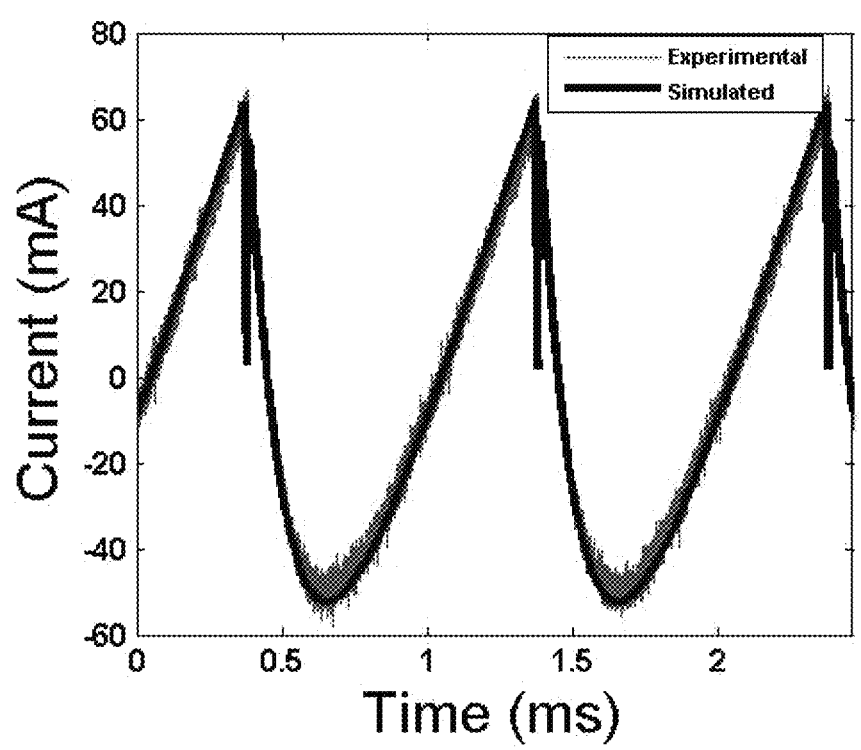
FIG. 15 illustrates a chart showing the total current through the electromagnetic coil used in the transmembrane assay experiments discussed herein.

In the described embodiment, the current through the coil is measured using a sense resistance of 1.25Ω with the function generator supplying a 20 Vpp sawtooth waveform at 1 kHz (FIG. 15). Also shown in the figure is the coil conduction current calculated using the circuit element model (FIG. 14). The intrinsic coil capacitance was determined by parametric variation to be 30 nF using the measured values (at 1 kHz) of 50.45Ω for the d.c. resistance and 14.25 mH for the inductance. Varying the intrinsic coil capacitance alters the magnitude of the spike whereas the inductance and resistance together shift the bowl shaped profile for all other times in the period (FIG. 15). As can be seen, the agreement between prediction and measurement is excellent.

Figure 16:
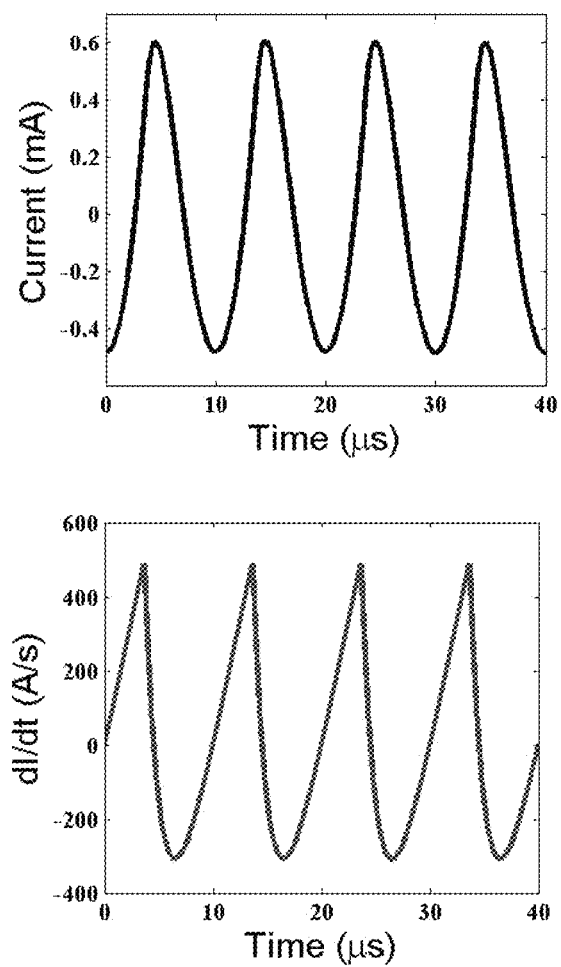
FIG. 16 illustrates a chart showing predicted current (top) through the electromagnetic coil used in the transmembrane assay experiments at a duty cycle of 100 kHz for a 20 Vpp sawtooth voltage waveform, and its derivative (bottom)

The circuit element model is used to predict the current at 100 kHz using the same values of inductance, resistance, and capacitance at 1 kHz. The resulting current as a function of time exhibits asymmetry over a period (FIG. 16). The induced electric field is proportional to dI/dt (equation (6)) and is therefore also asymmetric over any given period.

Figure 17:
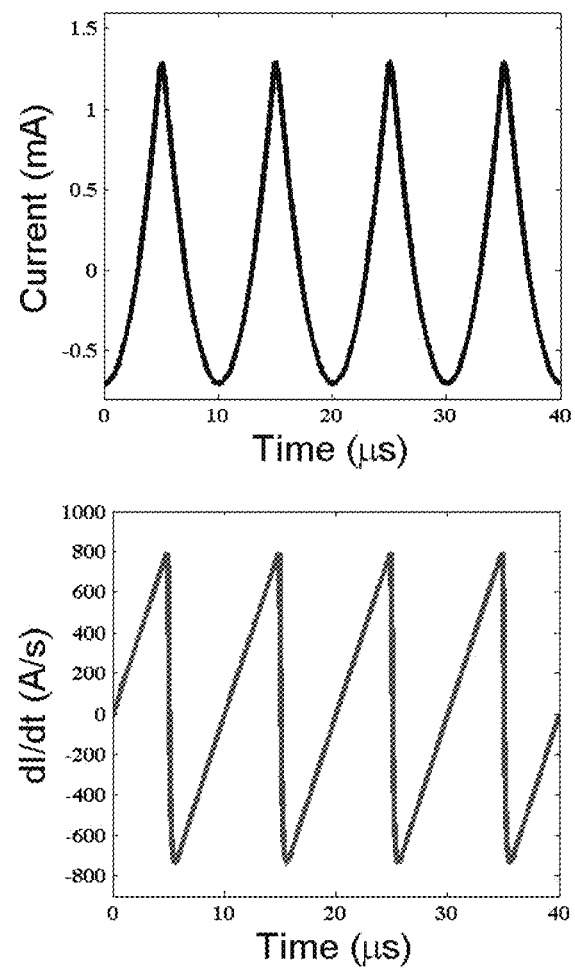
FIG. 17 illustrates a chart showing predicted current through the electromagnetic coil used in the actin filament imaging experiments, at a duty cycle of 100 kHz for a 20 Vpp sawtooth voltage waveform.

Analysis of induced electric fields in visualization of actin filaments: in the following embodiment, for the purpose of visualizing actin filaments using phalloidin and fluorescence microscopy, the orientation of the coil is changed compared to the configuration used in the transmembrane assay experiments. The electromagnetic coil used to generate the induced electric fields in these methods also consists of multiple windings (18 layers, ~67 turns per layer) of insulated 32 AWG (0.268 mm diameter with insulation or 0.202 mm diameter bare) wire. The inner diameter of the coil is 14.2 mm, the outer diameter is 2.332 cm, and its length is 2.47 cm. Measurements of the coil resistance and inductance using an LCR meter (Extech Instruments Model 380193) yields 24.58Ω and 12.17 mH, respectively, at 1 kHz. The coil is placed at the center of the holder with a standard 60 mm diameter culture plate on top (FIG. 17, FIG. 5a). The physical characteristics of the coil (wire gage, diameter, number of turns, length, number of layers) given here are for the methods and embodiments discussed herein. It is appreciated that these parameters as well as the duty cycle of the imposed voltage (which is 100 kHz for this embodiment) can all be changed depending on the desired effects. It is important to ensure that the function generator (Hewlett Packard 33120A used in the present experiments) is able to drive sufficient current through the coil. In a similar manner, the holder can also be easily modified to accommodate a multi-well plate (FIG. 12). Currents through the coil and the resulting magnetic inductions and induced electric fields can be calculated as described by equations (4)-(6) in the previous section for a 20 Vpp sawtooth voltage waveform at a duty cycle of 100 kHz (FIG. 17, FIGS. 5b-5d).

Analysis of actin filament distribution: images obtained from phalloidin and fluorescence microscopy are imported into MATLAB (2014a, Mathworks, Inc., Massachusetts, U.S.A.). Individual cells are isolated and re-oriented so that their longest dimension is in the horizontal direction. Intensities are then separated into red, green, and blue so that the background and nuclei intensities may be filtered out and only the green fluorescence from the actin filaments is extracted. Actin fluorescence intensities are analyzed versus cell length (longer dimension being the length), and averaged. These post-processed images and average intensities for the isolated cells shown in FIG. 6, are shown in FIGS. 18-20.

Figure 21:
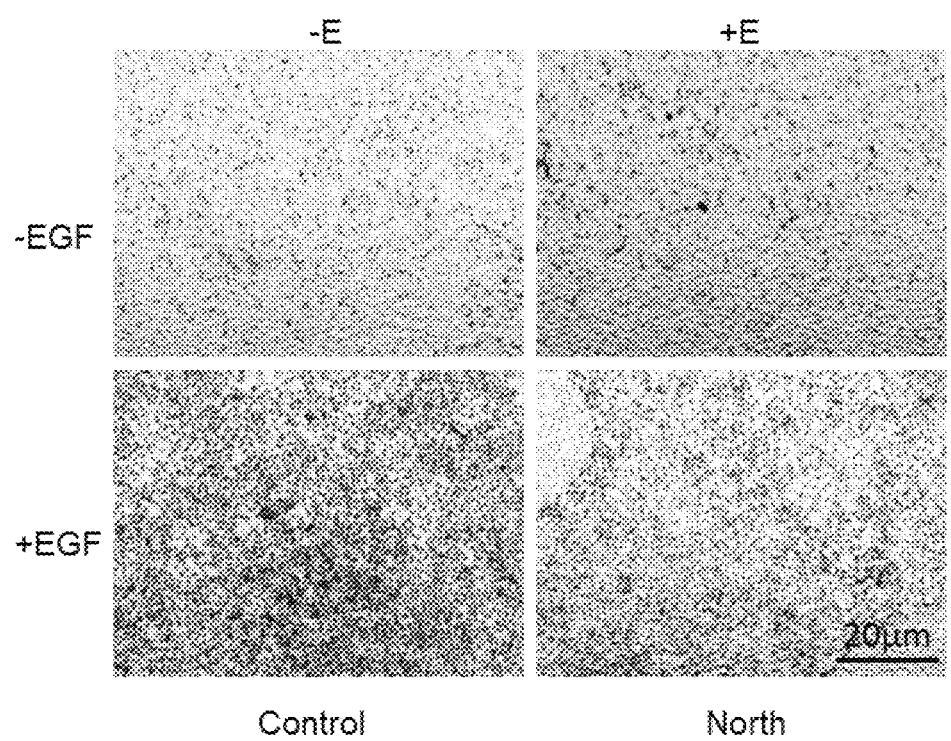
FIG. 21 illustrates representative fields of view from the modified transmembrane assay with a Transwell membrane with MCF-10A cells fixed and stained, showing how the cells are counted.

Experimental results for "normal" breast epithelial cells (MCF-10A): in the following described embodiment, experiments on combined chemotaxis and electrotaxis performed with MCF10A cells in the modified transmembrane assay utilized the growth factor EGF in the lower compartment of the modified transmembrane assay. After allowing 16 hours of incubation in the modified transmembrane assay, the cells that migrated to the other side of the Transwell membrane in the top chamber were stained with Hema 3 stain kit (Fisher Scientific, 122-911) according to the manufacturer's instructions. The stained cells were then photographed with a Zeiss microscope attached to a camera. The migrated cells were counted in five representative fields. As an illustration, representative fields are shown in FIG. 21. Data for migration of MCF-10A cells with and without growth factor EGF and with and without induced electric fields, is shown in FIG. 22. As can be seen from FIGS. 21-22, MCF-10A cells hardly migrate without the presence of EGF (control in FIG. 22), and the presence of an electric field in the direction of migration ("North" side) has no statistically significant effect in this case in the absence of EGF (Coil North+E−EGF in FIG. 22). On the other hand, it can be seen that EGF strongly promotes migration of MCF-10A cells (−E+EGF in FIG. 22) and the induced electric field hinders their migration (Coil North+E+EGF in FIG. 22) with statistical significance (p=0.002) for −E+EGF versus Coil North+E+EGF in FIG. 22).

The glass wells illustrated in FIG. 7 are configured to accommodate commercially available Transwell transmembrane inserts. The outer compartment and holder (FIG. 8) are designed so that the membrane (the bottom surface of the inner funnel) is as close as possible to the outer surface of the coil, to within 1 mm.

The holder is preferably fabricated using 3-D printing technology after first developing a computer-aided design (CAD) drawing using the software SolidWorks. The circular wells in the holder preferably have unique dimensions based on the exact dimensions of each glass well (FIG. 7). In one embodiment, the center channel of the holder allows the coil to be placed in the center so that there are three wells each on either side of the coil.

FIG. 9 illustrates representative fields (4 each) from the Transwell transmembrane assay and the modified transmembrane assay with SCP2 cells fixed and stained, showing how the cells are counted in one embodiment of the invention. The cells were allowed to migrate for 8 hours, and were fixed and stained using Hema-3 stain kit according to the manufacturer's instructions. The number of migratory cells per membrane was then measured using light microscopy by counting the total number of cells in each of five contiguous images taken at 20× magnification, spanning radially outward (five fields) from the coil. The counts were used to determine the percentage of migration. Only a representative set of control images are shown as there was no statistically significant difference between the control on the "North" and "South" sides.

FIG. 10 illustrates how the modified transmembrane assay with the Transwell membrane inserts reproduces cell migration observed in the presently used multi-well plates with the same inserts. These cell migration experiments were performed over a period of 8 hours on SCP2 cells (N=3). No induced electric field was applied and the same media (0.1% FBS-DMEM) was used (p=0.993).

FIG. 10 illustrates one embodiment of a modified holder, coil, and culture plate used in the experiments to image actin filaments using phalloidin and fluorescence microscopy. The holder is preferably fabricated using 3-D printing technology after first developing a computer-aided design (CAD) drawing using the software SolidWorks.

FIG. 12 illustrates how a modified assembly for accommodating a culture plate may be altered for a 96 well multi-well plate. The holder is preferably fabricated using 3-D printing technology after first developing a computer-aided design (CAD) drawing using the software SolidWorks.

FIG. 13 illustrates one embodiment of a circuit diagram showing the use of a sense resistor to measure the current through the coil. The coil has a d.c. resistance, inductance, and intrinsic capacitance (FIG. 14). Consequently, measurement of the current in the circuit by placing the sense resistance downstream of the coil, and measuring the voltage drop yields the total current flow (sum of conduction and displacement currents through the coil). This measurement at 1 kHz allows the intrinsic capacitance to be inferred by comparing the measured voltage trace across the sense resistance with a voltage trace predicted by a circuit element model that simulates the coil as a resistor in series with an inductor, both of which are in parallel with a capacitor (FIG. 14). This intrinsic coil capacitance is then used to calculate the conduction current at 100 kHz, relevant for the electrotaxis experiments. The current measurement described herein is sensitive to stray capacitances that can arise from coax connectors (such as tees) placed at the oscilloscope. Therefore, care must be exercised to eliminate such sources of stray capacitance. Ultimately, a check of the measurement can be accomplished as the current measured with the sense capacitance placed upstream of the coil should yield a similar current as when the sense capacitance is placed downstream of the coil.

FIG. 14 illustrates one embodiment of a circuit diagram showing a model used to predict the current through the coil. This circuit element model is used to predict the total current through the coil at 1 kHz, and to compare it with the current measurement using the sense resistance (FIG. 13) at 1 kHz. This enables the intrinsic coil capacitance to be inferred (30 nF) by matching the prediction with measurement at 1 kHz. This value of the intrinsic coil capacitance is then used to predict the conduction current through the coil at the experimental duty cycle of 100 kHz.

FIG. 15 illustrates a chart showing the total current through the electromagnetic coil used in the transmembrane assay experiments discussed herein (measured in red, calculated in black) at a duty cycle of 1 kHz for a 20 Vpp sawtooth voltage waveform. By systematically varying only the intrinsic coil capacitance until the prediction matches the measurement yields a value of 30 nF. The spike in the figure is due to the displacement current passing through the coil capacitance. This inferred value of the intrinsic coil capacitance is then used to predict the conduction current through the coil at 100 kHz.

FIG. 16 illustrates a chart showing predicted current (top) through the electromagnetic coil used in the transmembrane assay experiments, at a duty cycle of 100 kHz for a 20 Vpp sawtooth voltage waveform, and its derivative (bottom). It can be seen that the derivative of the current through the coil is asymmetric over a single period of the duty cycle so that the electric field is in the downward direction on the "South" and "North" sides of the coil for different durations (~40% on the "South" side and ~60% on the "North" side).

FIG. 17 illustrates a chart showing predicted current through the electromagnetic coil used in the actin filament imaging experiments, at a duty cycle of 100 kHz for a 20 Vpp sawtooth voltage waveform. It can be seen that the derivative of the current through the coil is approximately symmetric over a single period of the duty cycle so that the electric field is in the leftward and rightward directions for different durations on the culture plate (when viewed from the top) (FIGS. 5b-5e).

FIGS. 18a and 18b illustrate charts showing the average intensity of actin fluorescence versus length along isolated cells shown in the left panel of FIG. 6a. The actin cytoskeleton in SCP2 cells in the absence of both EGF and induced electric fields is quantified here and averaged to show the distribution of fluorescence intensity versus length along the cell. Also shown in the upper right images of both panels (A) and (B) are the filtered images displaying only the actin cytoskeleton.

FIGS. 19a and 19b illustrate charts showing the average intensity of actin fluorescence versus length along isolated cells shown in the middle panel of FIG. 6a. The actin cytoskeleton in SCP2 cells in the presence of EGF and without induced electric fields is quantified here and averaged to show the distribution of fluorescence intensity versus length along the cell. Also shown in the upper right images of both panels (A) and (B) are the filtered images displaying only the actin cytoskeleton.

Figure 20A:
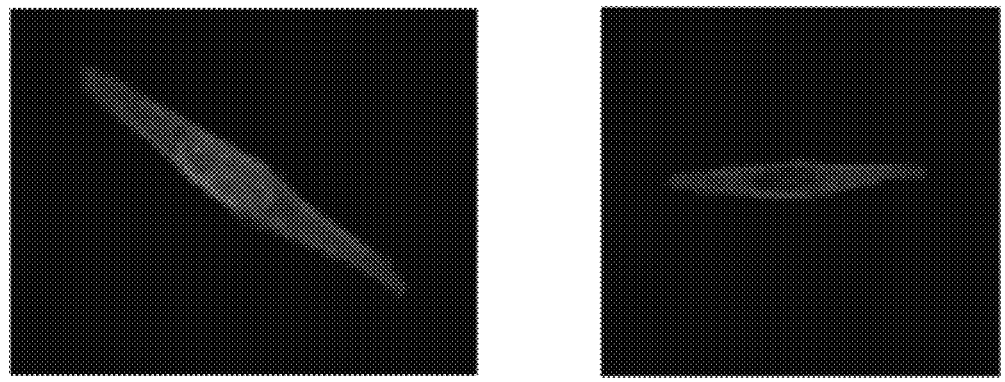
Figure 20A:
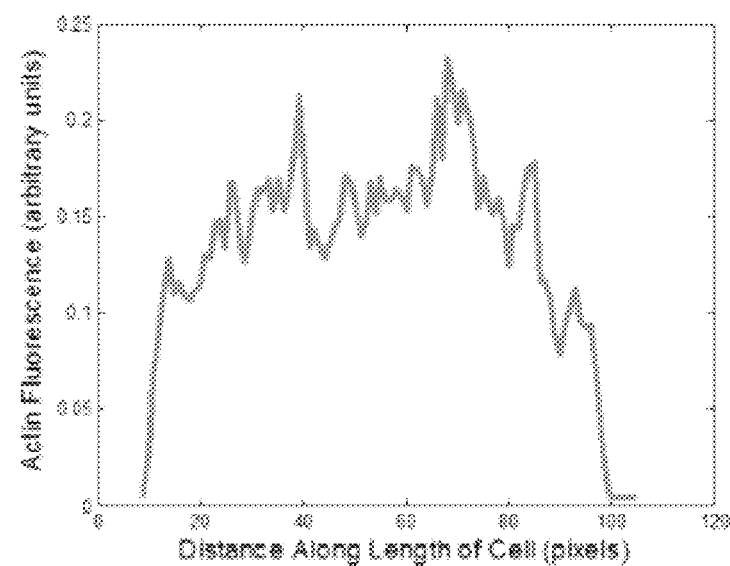
Figure 20B:
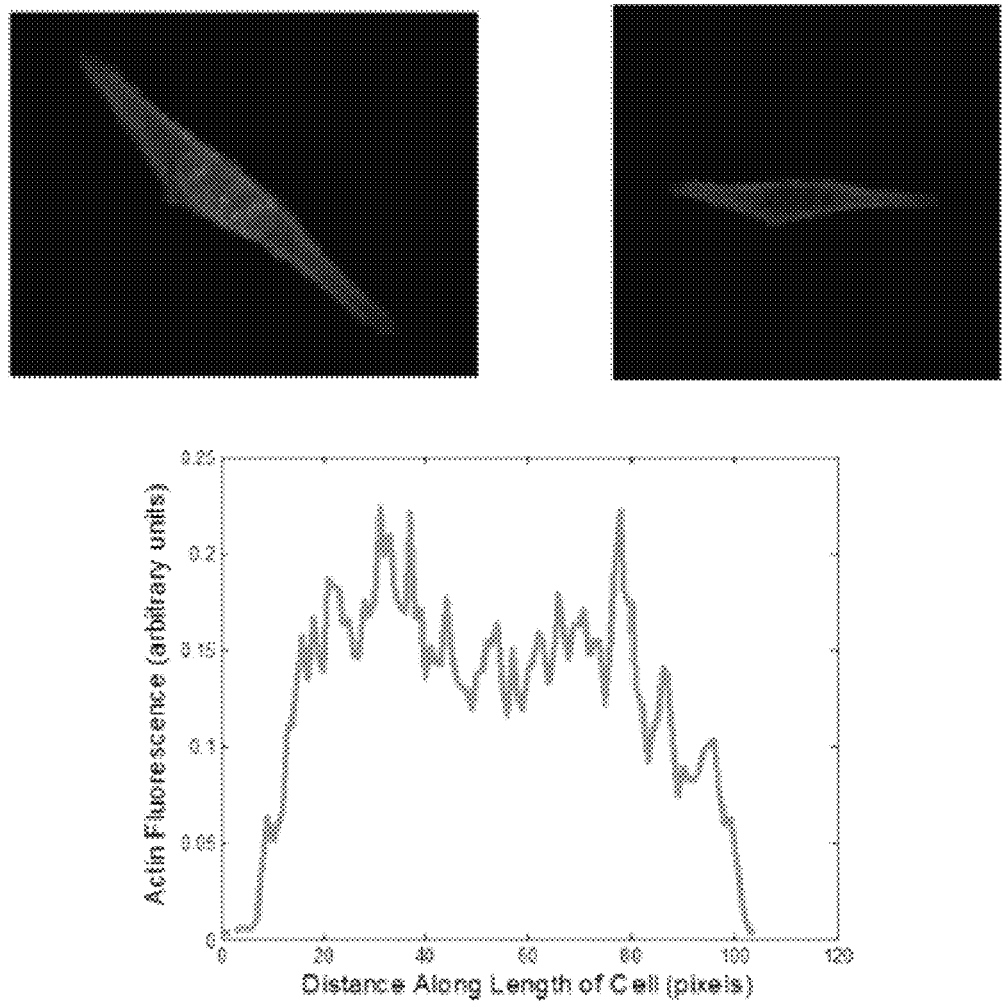
Figure 20C:
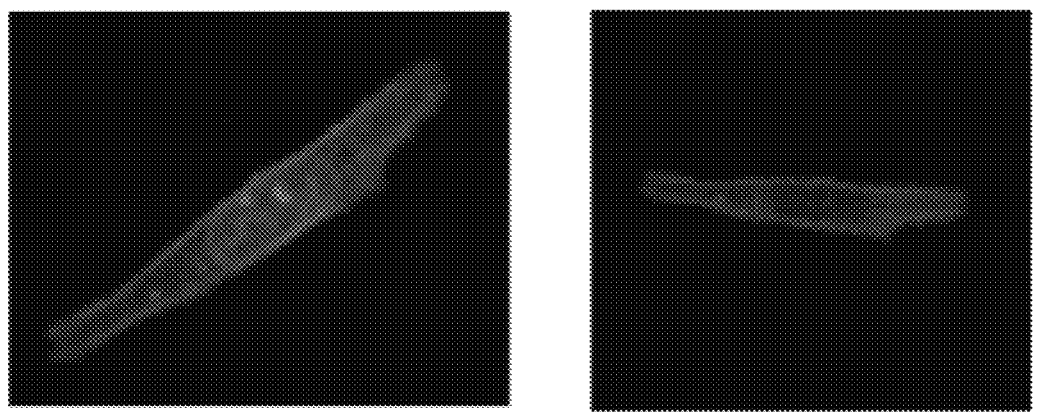
Figure 20C:
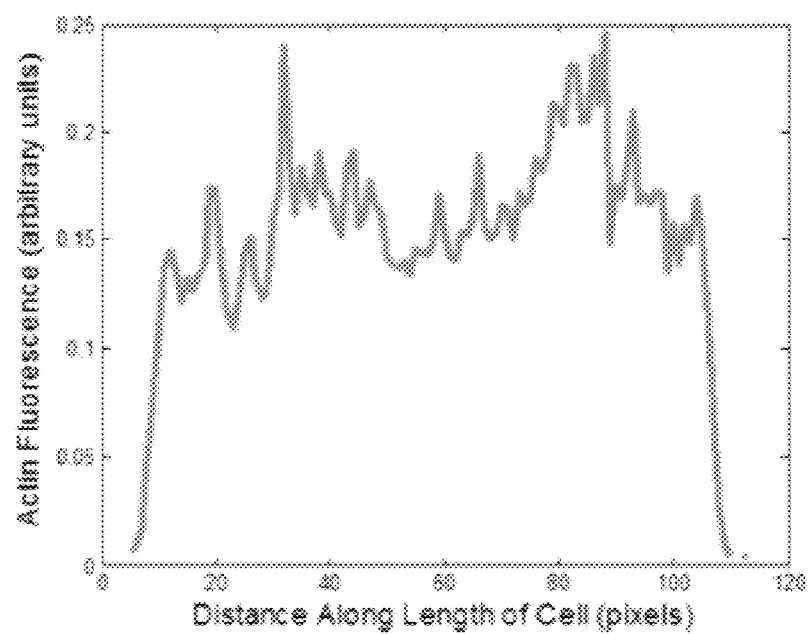

FIGS. 20a through 20c illustrate charts showing the average intensity of actin fluorescence versus length along isolated cells shown in the right panel of FIG. 6a. The actin cytoskeleton in SCP2 cells in the presence of both EGF and induced electric fields is quantified here and averaged to show the distribution of fluorescence intensity versus length along the cell. Also shown in the upper right images of panels (A), (B), and (C) are the filtered images displaying only the actin cytoskeleton.

FIG. 21 illustrates representative fields from the modified transmembrane assay with a Transwell membrane with MCF-10A cells fixed and stained, showing how the cells are counted. In this embodiment, the cells were allowed to migrate for 16 hours, and were fixed and stained using Hema-3 stain kit according to the manufacturer's instructions. The number of migratory cells per membrane was then measured using light microscopy by counting the total number of cells in each of five contiguous images spanning radially outward (five fields) from the coil. The counts were used to determine the percentage of migration.

FIG. 22 illustrates a chart showing a summary of experimental results of migration of MCF-10A cells in the modified transmembrane assay showing the effects of induced electric fields with and without the growth factor EGF. These cell migration experiments were performed over a period of 16 hours on MCF-10A cells. These experiments were performed on the same apparatus and under the same conditions as in FIG. 4. Column 1: Control without induced E fields or EGF in the modified transmembrane assay (N=2). Column 2: Effect of induced E fields on MCF-10 cells in the absence of EGF on the "North" side of the modified transmembrane assay (N=2). Column 3: Control in the modified transmembrane assay with a Transwell insert, without induced E fields but in the presence of growth factor EGF in the lower chamber (N=4). Column 4: Migration is hindered on the "North" side of the coil in the presence of both EGF and induced electric fields (Column 3 versus Column 4: p=0.002), where for the majority (60%) of the 10 □s period, the induced E field is in the direction of migration (i.e. directed downward) (N=4).

While certain embodiments of the present invention are described in detail above, the scope of the invention is not to be considered limited by such disclosure, and modifications are possible without departing from the spirit of the invention as evidenced by the following claims:

What is claimed is:

1. A method for controlling cell migration comprising the steps of:
   providing an electromagnetic coil having a first end and a second end;
   connecting the electromagnetic coil to a function generator;
   applying a time-varying voltage waveform to the electromagnetic coil, wherein the time-varying voltage waveform has a sharp drop off at its trailing edge and wherein the induced electric field is a rapidly time-varying magnetic field;
   inducing a time-varying electric field around the electromagnetic coil;
   placing the electromagnetic coil adjacent to, and without contacting, the location of cells;
   hindering the migration of the cells using the induced electric field.

2. A method according to claim 1 further comprising the steps of:
   inducing eddy currents near the location of the cells; and
   varying the direction and spatial extent of the induced electric field enabling different cells to migrate at different times.

3. A method according to claim 1, wherein the time-varying waveform is a sawtooth waveform.

4. A method according to claim 1, wherein the time-varying waveform is a 20 volts peak to peak, 100 kHz sawtooth waveform with a 50 ns drop off at its trailing edge.

5. A method according to claim 1, further comprising the step of: applying the induced electric field in a direction of cell migration.

6. A method according to claim 1, further comprising the steps of:
   placing the electromagnetic coil in between a first row of a plurality of assay wells and second row of a plurality of assay wells;
   providing a plurality of well inserts having a porous membrane;
   placing one of the well inserts into each of the plurality of assay wells so that the wells are divided into a lower and upper compartment;
   placing a medium into each of the plurality of assay wells;
   placing a predetermined line of cancer cells into each of the assay wells; and
   allowing the predetermined lines of cancer cells to settle on top of the porous membranes.

7. A method according to claim 6, further comprising the step of:
   introducing a predetermined chemokine into each of the assay wells.

8. A method for controlling cancer cell migration comprising the steps of:
   providing an electromagnetic coil having a first end and a second end;
   connecting the electromagnetic coil to a function generator;
   applying a time-varying voltage waveform to the electromagnetic coil;
   selecting the diameter, shape and size of the coil so that the induced electric field is uniform over a desired region;
   inducing a time-varying electric field around the electromagnetic coil;
   placing the electromagnetic coil adjacent to, and without contacting, the location of cancer cells; and
   hindering migration of the cancer cells using the induced electric field.

9. A method according to claim 8, wherein the time-varying waveform is a 20 volts peak to peak, 100 kHz sawtooth waveform with a 50 ns drop off at its trailing edge.

10. A method according to claim 8, further comprising the step of varying the direction and spatial extent of the induced electric field enabling different cells to migrate at different times.

11. A method according to claim 8, further comprising the steps of:
placing the electromagnetic coil in between a first row of a plurality of assay wells and second row of a plurality of assay wells;
providing a plurality of well inserts having a porous membrane;
placing one of the well inserts into each of the plurality of assay wells so that the wells are divided into a lower and upper compartment;
placing a medium into each of the plurality of assay wells;
placing a predetermined line of cancer cells into each of the assay wells; and
allowing the predetermined lines of cancer cells to settle on top of the porous membranes.

12. A method according to claim 11, further comprising the steps of:
taking an image of the porous membrane after the step of inducing a time-varying electric field; and
quantifying metastatic potential of the predetermined lines of cancer cells.

13. A method according to claim 8, further comprising the step of:
orientating the placement of the electromagnetic coil so that the direction of the electric field is applied in a direction of migration of the cancer cells.

14. A method according to claim 1, wherein the coil has multiple layers of windings with an outer diameter larger than an inner diameter.

15. A method according to claim 8, wherein the coil has multiple layers of windings with an outer diameter larger than an inner diameter.

16. A method according to claim 1, further comprising the step of selecting the diameter, shape and size of the coil to exert a particular value of the induced electric field at specific locations located radially from the coil.

17. A method according to claim 8, further comprising the step of selecting the diameter, shape and size of the coil to exert a particular value of the induced electric field at specific locations located radially from the coil.

18. A method according to claim 1, wherein the induced electric field is asymmetric over a duty cycle.

19. A method according to claim 8, wherein the induced electric field is asymmetric over a duty cycle.

20. A method according to claim 1, further comprising the steps of:
measuring current through the coil using a sense resistance;
predicting the current through the coil and comparing it to the measured current;
predicting the coil conduction current for a predetermined voltage waveform at a higher frequency;
calculating the vector potential;
calculating the radial and axial components of magnetic induction;
calculating the induced electric field; and
using the calculated induced electric field to select a desired coil design.

21. A method according to claim 8, further comprising the steps of:
measuring current through the coil using a sense resistance;
predicting the current through the coil and comparing it to the measured current;
predicting the coil conduction current for a predetermined voltage waveform at a higher frequency;
calculating the vector potential;
calculating the radial and axial components of magnetic induction;
calculating the induced electric field; and
using the calculated induced electric field to select a desired coil design.

22. A method according to claim 1, wherein the induced electric field has a magnitude on the order of 1 microvolt/cm or less.

23. A method according to claim 8, wherein the induced electric field has a magnitude on the order of 1 microvolt/cm or less.

24. A method according to claim 5, wherein the time-varying waveform induces an electric field in the direction of migration for a greater duration than in a direction opposite to the direction of migration.

25. A method according to claim 13, wherein the time-varying sawtooth waveform induces an electric field in the direction of migration for a greater duration than in a direction opposite to the direction of migration.

26. A method for controlling cell migration comprising the steps of:
providing an electromagnetic coil having a first end and a second end;
connecting the electromagnetic coil to a function generator;
applying a time-varying voltage waveform to the electromagnetic coil;
inducing a time-varying electric field around the electromagnetic coil, wherein the induced electric field has a magnitude on the order of 1 microvolt/cm or less;
placing the electromagnetic coil adjacent to, and without contacting, the location of cells; and
hindering the migration of the cells using the induced electric field.

27. A method according to claim 26, wherein the time-varying waveform is a sawtooth waveform having a sharp drop off at its trailing edge.

28. A method according to claim 26, further comprising the step of:
applying the induced electric field in a direction of cell migration; and
wherein the time-varying waveform induces an electric field in the direction of migration for a greater duration than in a direction opposite to the direction of migration.

29. A method according to claim 26, further comprising the step of selecting the diameter, shape and size of the coil to exert a particular value of the induced electric field at specific locations located radially from the coil.

30. A method according to claim 26, wherein the time-varying waveform is a 20 volts peak to peak, 100 kHz sawtooth waveform with a 50 ns drop off at its trailing edge; and
wherein the induced electric field is a rapidly time-varying magnetic field.

* * * * *